(12) United States Patent
Gobbi et al.

(10) Patent No.: US 6,727,261 B2
(45) Date of Patent: Apr. 27, 2004

(54) PYRIDO[2,1-A]ISOQUINOLINE DERIVATIVES

(75) Inventors: Luca Claudio Gobbi, Oberwil (CH); Thomas Luebbers, Loerrach (DE); Patrizio Mattei, Riehen (CH); Robert Narquizian, Bartenheim (FR); Pierre Charles Wyss, Therwil (CH)

(73) Assignee: Hoffman-La Roche Inc., Nutley, NJ (US)

(*) Notice: Subject to any disclaimer, the term of this patent is extended or adjusted under 35 U.S.C. 154(b) by 0 days.

(21) Appl. No.: 10/321,692

(22) Filed: Dec. 17, 2002

(65) Prior Publication Data

US 2003/0149071 A1 Aug. 7, 2003

(30) Foreign Application Priority Data

Dec. 27, 2001 (EP) .............................................. 01130882

(51) Int. Cl.⁷ ................ A61K 31/4375; A61K 31/4745; C07D 471/02
(52) U.S. Cl. ............................ 514/294; 546/96; 546/94; 546/71
(58) Field of Search ................................. 514/294, 284; 546/95, 94, 71

(56) References Cited

FOREIGN PATENT DOCUMENTS

| WO | WO 98/19998 | 5/1998 |
|----|-------------|--------|
| WO | WO 02 074042 | 9/2002 |

OTHER PUBLICATIONS

RN 39630–39–2, 39630–42–7 (discloded in 1972) and 109964–42–3 (disclosed in 1957).*
M. Hirotoshi, Patent Abstracts of Japan, JP 11 230910, vol. 1999, NO. 13 (1999).
D. J. Canney, et al., Nucl. Med. Biol., XP002238994, vol. 22, No. 4, pp. 527–535 (1995).
D. Scherman, et al., Chemical Abstracts XP002238995, vol. 108, No. 17, p. 124 (1988).
M. F. Isamert, J. P. Henry, Chemical Abstracts XP002238996, vol. 103, No. 5, p. 243 (1985).
A. Buzas, et al., Chemical Abstracts XP002238997, vol. 78, No. 7, p. 466 (1973).
A.R. Battersby, et al., Chemical Abstracts XP002238998, vol. 54, No. 13, p. 982 (1960).
J. M. Fox et al., J. Am. Chem. Soc. 2000, vol. 122 pp. 1360–1370 (Supporting Information pp. 2–32).
M. Kawatsura et al., J. Am. Chem Soc. 1999, vol. 121, pp. 1473–1478.
Translation of the claims of JP Publication No. 11230910.
Isambert, Marie–Francoise, et al., Biochemistry, vol. 28, No. 5, pp. 2265–2270(1989).

* cited by examiner

*Primary Examiner*—Charanjit S. Aulakh
(74) *Attorney, Agent, or Firm*—George W. Johnston; Dennis P. Tramaloni; Eileen M. Ebel

(57) ABSTRACT

The present invention provides compounds of formula (I)

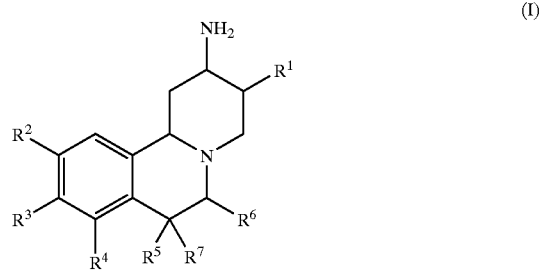

(I)

wherein $R^1$, $R^2$, $R^3$, $R^4$, $R^5$ and $R^6$ are as defined in the specification, and pharmaceutically acceptable salts thereof. The compounds are useful for the treatment and/or prophylaxis of diseases which are associated with DPP-IV, such as diabetes, particularly non-insulin dependent diabetes mellitus, and impaired glucose tolerance.

17 Claims, No Drawings

PYRIDO[2,1-A]ISOQUINOLINE DERIVATIVES

BACKGROUND OF THE INVENTION

The enzyme dipeptidyl peptidase IV (EC.3.4.14.5, abbreviated in the following as DPP-IV) is involved in the regulation of the activities of several hormones. In particular DPP-IV is degrading efficiently and rapidly glucagon like peptide 1 (GLP-1), which is one of the most potent stimulator of insulin production and secretion. Inhibiting DPP-IV would potentiate the effect of endogenous GLP-1, and lead to higher plasma insulin concentrations. In patients suffering from impaired glucose tolerance and type 2 diabetes mellitus, higher plasma insulin concentration would moderate the dangerous hyperglycaemia and accordingly reduce the risk of tissue damage. Consequently, DPP-IV inhibitors have been suggested as drug candidates for the treatment of impaired glucose tolerance and type 2 diabetes mellitus (e.g. Vilhauer, WO98/19998). Without disclosing any medical use, Buzas et al., Lab. Chim. Org. V, Fac. Sci., Orleans, Fr. Chim. Ther. (1992), 7(5), 404–7 describe synthesis of the compounds of Examples 41 and 42 below.

SUMMARY OF THE INVENTION

The compounds of the present invention are useful for the treatment and/or prophylaxis of diabetes or non-insulin dependent diabetes.

The present invention provides pyrido[2,1-a]isoquinoline derivatives in accordance with formula (I)

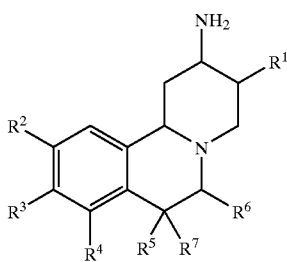

wherein
- $R^1$ is lower alkyl, aryl, substituted aryl, heteroaryl, substituted heteroaryl, or lower alkyl substituted by cycloalkyl, aryl, substituted aryl, heteroaryl or substituted heteroaryl;
- $R^2$, $R^3$ and $R^4$ are each independently hydrogen, halogen, hydroxy, lower alkyl, lower alkoxy or lower alkenyl, wherein lower alkyl, lower alkoxy and lower alkenyl are optionally substituted by lower alkoxycarbonyl, aryl, substituted aryl, heterocyclyl or substituted heterocyclyl;
- $R^5$ is hydrogen, fluorine, lower alkyl, aryl or substituted aryl;
- $R^6$ is hydrogen, lower alkyl or hydroxy-lower alkyl, or
- $R^5$ and $R^6$ together with the carbon atoms to which they are attached form a five or six membered saturated carbocyclic ring;
- $R^7$ is hydrogen, fluorine or lower alkyl;
- and pharmaceutically acceptable salts thereof;
- with the exception of rac-3β-Isobutyl-9,10-dimethoxy-1,3,4,6,7,11bβ-hexahydro-2H-pyrido[2,1-a]isoquinolin-2β-ylamine dihydrochloride and rac-3β-Isobutyl-9,10-dimethoxy-1,3,4,6,7,11bβ-hexahydro-2H-pyrido[2,1-a]isoquinolin-2α-ylamine dihydrochloride.

DETAILED DESCRIPTION OF THE INVENTION

Novel DPP-IV inhibitors have been found that very efficiently lower plasma glucose levels. Consequently, the compounds of the present invention are useful for the treatment and/or prophylaxis of diabetes, particularly non-insulin dependent diabetes mellitus, and/or impaired glucose tolerance, as well as other conditions wherein the amplification of action of a peptide normally inactivated by DPP-IV gives a therapeutic benefit. Surprisingly, the compounds of the present invention can also be used in the treatment and/or prophylaxis of Bowl disease, Colitis Ulcerosa, Morbus Crohn, obesity and/or metabolic syndrome. Furthermore, the compounds of the present invention can be used as diuretic agents and for the treatment and/or prophylaxis of hypertension. Unexpectedly, the compounds of the present invention exhibit improved therapeutic and pharmacological properties compared to other DPP-IV inhibitors known in the art, such as e.g. in context with pharmacokinetics and bioavailability.

The present invention provides pyrido[2,1-a]isoquinoline derivatives in accordance with formula (I)

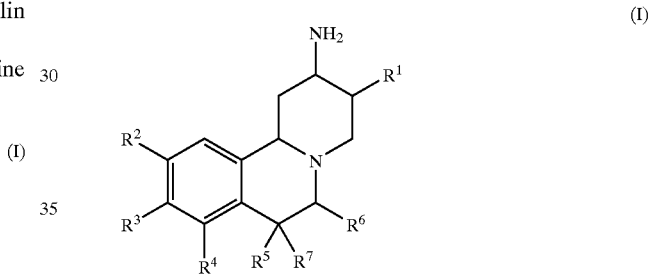

wherein
- $R^1$ is lower alkyl, aryl, substituted aryl, heteroaryl, substituted heteroaryl, or lower alkyl substituted by cycloalkyl, aryl, substituted aryl, heteroaryl or substituted heteroaryl;
- $R^2$, $R^3$ and $R^4$ are each independently hydrogen, halogen, hydroxy, lower alkyl, lower alkoxy or lower alkenyl, wherein lower alkyl, lower alkoxy and lower alkenyl are optionally substituted by lower alkoxycarbonyl, aryl, substituted aryl, heterocyclyl or substituted heterocyclyl;
- $R^5$ is hydrogen, fluorine, lower alkyl, aryl or substituted aryl;
- $R^6$ is hydrogen, lower alkyl or hydroxy-lower alkyl, or
- $R^5$ and $R^6$ together with the carbon atoms to which they are attached form a five or six membered saturated carbocyclic ring;
- $R^7$ is hydrogen, fluorine or lower alkyl;
- and pharmaceutically acceptable salts thereof;
- with the exception of rac-3β-Isobutyl-9,10-dimethoxy-1,3,4,6,7,11bβ-hexahydro-2H-pyrido[2,1-a]isoquinolin-2β-ylamine dihydrochloride and rac-3β-Isobutyl-9,10-dimethoxy-1,3,4,6,7,11bβ-hexahydro-2H-pyrido[2,1-a]isoquinolin-2α-ylamine dihydrochloride.

Unless otherwise indicated, the following definitions are set forth to illustrate and define the meaning and scope of the various terms used to describe the invention herein. In this specification the term "lower" is used to mean a group consisting of one to six, preferably of one to four carbon atom(s).

The term "halogen" refers to fluorine, chlorine, bromine and iodine, preferably to chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower-alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "cycloalkyl" refers to a monovalent carbocyclic radical of three to six carbon atoms. This term is further exemplified by radicals such as cyclopropyl, cyclobutyl, cyclopentyl and cyclohexyl, with cyclopropyl being preferred.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy, with methoxy being especially preferred.

The term "lower alkoxycarbonyl" refers to the group R'—O—C(O)—, wherein R' is lower alkyl.

The term "heterocyclyl" refers to a 5- or 6-membered aromatic or saturated N-heterocyclic residue, which may optionally contain a further nitrogen or oxygen atom, such as imidazolyl, pyrazolyl, thiazolyl, phenyl, pyridyl, pyrimidyl, morpholino, piperazino, piperidino or pyrrolidino, preferably pyridyl, thiazolyl or morpholino. The term "substituted heterocyclyl" refers to a heterocyclyl that is mono-, di- or tri-substituted, independently, by lower alkyl, lower alkoxy, halo, cyano, azido, amino, di-lower alkyl amino or hydroxy. Preferable substituent is lower alkyl, with methyl being preferred.

The term "aryl" refers to an aromatic monovalent mono- or polycarbocyclic radical, such as phenyl or naphthyl, preferably phenyl. The term "substituted aryl" refers to an aryl that is mono-, di- or tri-substituted, independently, by lower alkyl, lower alkoxy, halo, cyano, azido, amino, di-lower alkyl amino or hydroxy.

The term "heteroaryl" refers to a 5- or 6-membered, unsaturated aromatic monovalent cyclic radical containing one to three, preferably one or two, heteroatoms independently selected from nitrogen, sulfur and oxygen, with nitrogen being preferred. Examples of heteroaryl residues are pyrrolyl, pyridinyl and pyrimidinyl, with pyrrolyl and pyridinyl being preferred. The term "substituted heteroaryl" refers to a heteroalkyl that is mono-, di- or tri-substituted, independently, by halogen, amino, perfluoro-lower alkyl, lower alkyl or lower alkoxy.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment, the present invention relates to a compound of formula (I) as defined above, wherein $R^1$ is lower alkyl, aryl, substituted aryl, or lower alkyl substituted by cycloalkyl, aryl or substituted aryl; $R^2$, $R^3$ and $R^4$ are each independently hydrogen, hydroxy, lower alkyl, lower alkoxy or lower alkenyl, wherein lower alkyl, lower alkoxy and lower alkenyl may optionally be substituted by lower alkoxycarbonyl, aryl, substituted aryl, heterocyclyl or substituted heterocyclyl; $R^5$ and $R^6$ are each independently hydrogen, lower alkyl, aryl, substituted aryl, or, together with the carbon atoms to which they are attached form a five or six membered saturated carbocyclic ring; and pharmaceutically acceptable salts thereof.

In another embodiment, the present invention relates to a compound of formula (I) as defined above, wherein $R^1$ is lower alkyl, phenyl, or cycloalkyl-lower alkyl; $R^2$, $R^3$ and $R^4$ are each independently hydrogen, hydroxy, lower alkoxy; or lower alkoxy substituted by aryl, substituted aryl, heterocyclyl, substituted heterocyclyl, or lower alkoxycarbonyl. Preferable aryl or substituted aryl residues in $R^2$, $R^3$ and $R^4$ are phenyl or phenyl substituted by di-lower alkyl amino or cyano. Preferable heterocyclyl or substituted heterocyclyl residues in $R^2$, $R^3$ and $R^4$ are morpholino, pyridyl, thiazolyl or thiazolyl substituted by lower alkyl. Preferable lower alkoxycarbonyl residues in $R^2$, $R^3$ and $R^4$ are ethoxycarbonylmethoxy.

In another preferable embodiment, the present invention relates to a compound of formula (I) as defined above, wherein $R^1$ is lower alkyl, phenyl, phenyl substituted by lower alkyl or by lower alkoxy, or $R^1$ is heteroaryl or substituted heteroaryl, such as where the heteroaryl residue is pyrrolyl and pyridinyl, or cycloalkyl-lower alkyl; $R^2$, $R^3$ and $R^4$ are each independently hydrogen, hydroxy, lower alkoxy; or lower alkoxy substituted by aryl, substituted aryl, heterocyclyl, substituted heterocyclyl, or lower alkoxycarbonyl; $R^5$ is hydrogen, lower alkyl or phenyl mono- or di-substituted by lower alkyl, lower alkoxy or halogen; $R^6$ is hydrogen, lower alkyl or hydroxy-lower alkyl; or $R^5$ and $R^6$ together with the carbon atoms to which they are attached form a five or six membered saturated carbocyclic ring; and $R^7$ is hydrogen or lower alkyl In one embodiment, residue $R^1$ is lower alkyl or lower alkyl substituted by cycloalkyl, preferably cyclopropyl. Preferable lower alkyl residues $R^1$ are n-propyl, n-butyl, isobutyl, 3-methylbutyl and 2-ethylbutyl, most preferred are n-propyl, n-butyl and 3-methylbutyl.

Preferable lower alkyl substituted by cycloalkyl is cyclopropylmethyl.

In another embodiment, $R^1$ is aryl or substituted alkyl, preferably in which the aryl residue is phenyl. Substituted aryl residues $R^1$ may be mono-, di- or tri-substituted aryl, independently, by lower alkyl, lower alkoxy or hydroxy, preferably by lower alkyl or lower alkoxy. Preferably, aryl residues $R^1$ are unsubstituted.

In still another embodiment, $R^1$ is a heteroaryl or substituted heteroaryl in which the heteroaryl residue is selected from pyridinyl, pyrimidinyl and pyrrolyl. Preferred are pyridinyl or pyrrolyl. Substituted heteroaryl residues $R^1$ may be mono-, di- or tri-substituted heteroaryl, independently, by lower alkyl, lower alkoxy, or hydroxy, preferably by lower alkyl or lower alkoxy. Preferably, heteroaryl residues $R^1$ are unsubstituted.

Most preferred $R^1$ are lower alkyl, preferably n-butyl, or unsubstituted phenyl.

In one preferable embodiment, residue $R^2$ is lower alkoxy, preferably methoxy, hydrogen or hydroxy. Most preferable residue $R^2$ is methoxy.

In another preferable embodiment, residue $R^3$ is lower alkoxy, with methoxy, ethoxy, propoxy, n-butoxy and isobutoxy being preferred, hydrogen, hydroxy; or lower alkoxy, preferably methoxy or ethoxy, substituted by aryl, substituted aryl, heterocyclyl, substituted heterocyclyl, or lower alkoxycarbonyl.

Preferable aryl or substituted aryl substituents in $R^3$ are unsubstituted phenyl or phenyl mono-substituted by di-lower alkyl amino, with dimethylamino being preferred, or by cyano. Most preferable aryl substituents in $R^3$ is unsubstituted phenyl.

More preferable residues $R^3$ are lower alkoxy, preferably methoxy, hydrogen or hydroxy. Most preferred residue $R^3$ is methoxy or hydroxy, with methoxy being especially preferred.

In another preferable embodiment, residue $R^4$ is lower alkoxy, preferably methoxy, hydrogen or hydroxy. Most preferable residue $R^4$ is hydrogen.

In one embodiment, $R^5$ is hydrogen, lower alkyl, with methyl being preferred, or aryl or substituted aryl.

Preferable aryl or substituted aryl residues $R^5$ are unsubstituted phenyl or phenyl mono-, di- or tri-substituted, independently, by lower alkyl, lower alkoxy or halogen. Most preferable aryl residue $R^5$ is unsubstituted phenyl.

In another embodiment, $R^6$ is hydrogen, lower alkyl, with methyl being preferred, or hydroxy-lower alkyl, with 2-hydroxy-ethyl being preferred. Preferably, $R^6$ is hydrogen.

In still another embodiment, $R^5$ and $R^6$ are hydrogen or, together with the carbon atoms to which they are attached, form a six membered saturated carbocyclic ring.

In one embodiment, $R^7$ is hydrogen, in another embodiment $R^7$ is lower alkyl, preferably methyl.

Preferred compounds of formula (I) are those selected from the group consisting of:

rac-9,10-dimethoxy-3β-propyl-1,3,4,6,7,11bβ-hexahydro-2H-pyrido[2,1-a]isoquinolin-2β-ylamine,
rac-9,10-dimethoxy-3β-(3-methyl-butyl)-1,3,4,6,7,11bβ-hexahydro-2H-pyrido[2,1-a] isoquinolin-2α-ylamine,
rac-3β-cyclopropylmethyl-9,10-dimethoxy-1,3,4,6,7,11bβ-hexahydro-2H-pyrido[2,1-a]isoquinolin-2β-ylamine,
rac-7β-butyl-11,12-dimethoxy-2,3,4,4a,6,7,8,9,9a,13bβ-decahydro-1H-pyrido[1,2-f]phenanthridin-8β-ylamine,
rac-3β-butyl-9,10-dimethoxy-1,3,4,6,7,11bβ-hexahydro-2H-pyrido[2,1-a]isoquinolin-2α-ylamine chlorohydrate (1:2),
rac-9,10-dimethoxy-3β-propyl-1,3,4,6,7,11bβ-hexahydro-2H-pyrido[2,1-a]isoquinolin-2β-ylamine chlorohydrate (1:2),
rac-7β-butyl-11,12-dimethoxy-2,3,4,4a,6,7,8,9,9a,13bβ-decahydro-1H-pyrido[1,2-f]phenanthridin-8β-ylamine chlorohydrate (1:2),
rac-2β-amino-3β-butyl-10-methoxy-1,3,4,6,7,11bβ-hexahydro-2H-pyrido[2,1-a]isoquinolin-9-ol chlorohydrate (1:2),
rac-2α-amino-3β-butyl-10-methoxy-1,3,4,6,7,11bβ-hexahydro-2H-pyrido[2,1-a]isoquinolin-9-ol chlorohydrate (1:2),
rac-2β-amino-3β-butyl-10-methoxy-1,3,4,6,7,11bβ-hexahydro-2H-pyrido[2,1-a]isoquinolin-9-ol,
rac-2α-amino-3β-butyl-10-methoxy-1,3,4,6,7,11bβ-hexahydro-2H-pyrido[2,1-a]isoquinolin-9-ol, and
rac-9,10-dimethoxy-3β-phenyl-1,3,4,6,7,11bβ-hexahydro-2H-pyrido[2,1-a]isoquinolin-2-ylamine,
and pharmaceutically acceptable salts thereof.

Further preferred compounds of formula (I) are those selected from the group consisting of:
rac-9,10-Dimethoxy-3β-pyrrol-1-yl-1,3,4,6,7,11bβ-hexahydro-2H-pyrido[2,1-a]isoquinolin-2α-ylamine,
rac-9,10-Dimethoxy-3β-p-tolyl-1,3,4,6,7,11bβ-hexahydro-2H-pyrido[2,1-a]isoquinolin-2β-ylamine,
rac-9,10-Dimethoxy-3β-p-tolyl-1,3,4,6,7,11bα-hexahydro-2H-pyrido[2,1-a]isoquinolin-2α-ylamine,
rac-9,10-dimethoxy-3β-(3,4-dimethyl-phenyl)-1,3,4,6,7,11bβ-hexahydro-2H-pyrido[2,1-a]isoquinolin-2β-ylamine chlorohydrate (1:2),
rac-9,10-dimethoxy-3β-(3,4-Dimethyl-phenyl)-1,3,4,6,7,11bβ-hexahydro-2H-pyrido[2,1-a]isoquinolin-2α-ylamine chlorohydrate (1:2),
rac-9,10-Dimethoxy-3β-(3-methoxy-phenyl)-1,3,4,6,7,11bβ-hexahydro-2H-pyrido[2,1-a]isoquinolin-2β-ylamine chlorohydrate (1:2),
rac-9,10-Dimethoxy-3β-(3-methoxy-phenyl)-1,3,4,6,7,11bβ-hexahydro-2H-pyrido[2,1-a]isoquinolin-2α-ylamine chlorohydrate (1:2),
rac-9,10-Dimethoxy-3β-pyridin-1,3,4,6,7,11bβ-hexahydro-2H-pyrido[2,1-a]isoquinolin-2β-ylamine chlorohydrate (1:2),
rac-9,10-Dimethoxy-3β-pyridin-1,3,4,6,7,11bβ-hexahydro-2H-pyrido[2,1-a]isoquinolin-2α-ylamine chlorohydrate (1:2),
rac-4-(2β-Amino-3β-butyl-9,10-dimethoxy-1,3,4,6,7,11bβ-hexahydro-2H-pyrido[2,1-a]isoquinolin-7β-yl)-phenol,
rac-3β-Butyl-9,10-dimethoxy-6-methyl-1,3,4,6,7,11bβ-hexahydro-2H-pyrido[2,1-a]isoquinolin-2-ylamine,
rac-3β-Butyl-7β-(4-chloro-phenyl)-9,10-dimethoxy-1,3,4,6,7,11bβ-hexahydro-2H-pyrido[2,1-a]isoquinolin-2α-ylamine,
rac-3β-Butyl-7α-(4-chloro-phenyl)-9,10-dimethoxy-1,3,4,6,7,11bβ-hexahydro-2H-pyrido[2,1-a]isoquinolin-2α-ylamine,
rac-3β-Butyl-7β-(3,4-dimethoxy-phenyl)-9,10-dimethoxy-1,3,4,6,7,11bβ-hexahydro-2H-pyrido[2,1-a]isoquinolin-2α-ylamine,
rac-3β-Butyl-9,10-dimethoxy-7,7-dimethyl-1,3,4,6,7,11bβ-hexahydro-2H-pyrido[2,1-a]isoquinolin-2α-ylamine,
rac-3β-Butyl-9,10-dimethoxy-7,7-dimethyl-1,3,4,6,7,11bβ-hexahydro-2H-pyrido[2,1-a]isoquinolin-2β-ylamine,
rac-7β-Butyl-11,12-dimethoxy-2,3,4,4aβ,6,7,8,9,9aα,13bβ-decahydro-1H-pyrido[1,2-f]phenanthridin-8β-ylamine,
rac-7β-Butyl-11,12-dimethoxy-2,3,4,4aβ,6,7,8,9,9aα13bβ-decahydro-1H-pyrido[1,2-f]phenanthridin-8α-ylamine,
rac-3β-Butyl-7α-(3,4-dimethoxy-phenyl)-9,10-dimethoxy-6α-methyl-1,3,4,6,7,11bβ-hexahydro-2H-pyrido[2,1-a]isoquinolin-2-ylamine,
rac-7β-Butyl-11,12-dimethoxy-13b-methyl-2,3,4,4aβ,8,6,7,8,9,9a,13b-decahydro-1H-pyrido[1,2-f]phenanthridin-8β-ylamine,
rac-9,10-Dimethoxy-3α-phenyl-1,3,4,6,7,11bα-hexahydro-2H-pyrido[2,1-a]isoquinolin-2α-ylamine,
rac-9,10-Dimethoxy-3α-phenyl-1,3,4,6,7,11bα-hexahydro-2H-pyrido[2,1-a]isoquinolin-2β-ylamine,
9,10-Dimethoxy-3α-phenyl-1,3,4,6,7,11bα-hexahydro-2H-pyrido[2,1-a]isoquinolin-2α-ylamine,
9,10-Dimethoxy-3α-phenyl-1,3,4,6,7,11bα-hexahydro-2H-pyrido[2,1-a]isoquinolin-2β-ylamine,
9,10-Dimethoxy-3β-phenyl-1,3,4,6,7,11bβ-hexahydro-2H-pyrido[2,1-a]isoquinolin-2β-ylamine,
9,10-Dimethoxy-3β-phenyl-1,3,4,6,7,11bβ-hexahydro-2H-pyrido[2,1-a]isoquinolin-2α-ylamine,
(6S)-(2-Amino-3-butyl-9,10-dimethoxy-1,3,4,6,7,11bβ-hexahydro-2H-pyrido[2,1-a]isoquinolin-6-yl)-methanol,
rac-4-(2β-Amino-3β-butyl-9,10-dimethoxy-1,3,4,6,7,11bβ-hexahydro-2H-pyrido[2,1-a]isoquinolin-7-yl)-phenol hydrochloride, rac-4-(2β-Amino-3β-butyl-9,10-dimethoxy-1,3,4,6,7,11bβ-hexahydro-2H-pyrido[2,1-a]isoquinolin-7β-yl)-phenol hydrochloride,
rac-3β-Butyl-9,10-dimethoxy-6-methyl-1,3,4,6,7,11bβ-hexahydro-2H-pyrido[2,1-a]isoquinolin-2-ylamine hydrochloride,
rac-3β-Butyl-7β-(4-chloro-phenyl)-9,10-dimethoxy-1,3,4,6,7,11bβ-hexahydro-2H-pyrido[2,1-a]isoquinolin-2α-ylamine hydrochloride,
rac-3β-Butyl-7α-(4-chloro-phenyl)-9,10-dimethoxy-1,3,4,6,7,11bβ-hexahydro-2H-pyrido[2,1-a]isoquinolin-2α-ylamine hydrochloride,
rac-3β-Butyl-7β-(3,4-dimethoxy-phenyl)-9,10-dimethoxy-1,3,4,6,7,11bβ-hexahydro-2H-pyrido[2,1-a]isoquinolin-2α-ylamine hydrochloride,
rac-3α-Butyl-7β-(3,4-dimethoxy-phenyl)-9,10-dimethoxy-1,3,4,6,7,11bβ-hexahydro-2H-pyrido[2,1-a]isoquinolin-2β-ylamine hydrochloride,
rac-3β-Butyl-7β-(3,4-dimethoxy-phenyl)-9,10-dimethoxy-1,3,4,6,7,11bβ-hexahydro-2H-pyrido[2,1-a]isoquinolin-2β-ylamine hydrochloride,
rac-3β-Butyl-7α-(3,4-dimethoxy-phenyl)-9,10-dimethoxy-1,3,4,6,7,11bβ-hexahydro-2H-pyrido[2,1-a]isoquinolin-2α-ylamine hydrochloride,
rac-3β-Butyl-9,10-dimethoxy-7β-(4-methoxy-phenyl)-1,3,4,6,7,11bβ-hexahydro-2H-pyrido[2,1-a]isoquinolin-2α-ylamine hydrochloride,
rac-3β-Butyl-9,10-dimethoxy-7β-(4-methoxy-phenyl)-1,3,4,6,7,11bβ-hexahydro-2H-pyrido[2,1-a]isoquinolin-2β-ylamine hydrochloride,
rac-3β-Butyl-9,10-dimethoxy-7,7-dimethyl-1,3,4,6,7,11bβ-hexahydro-2H-pyrido[2,1-a]isoquinolin-2α-ylamine hydrochloride,
rac-3β-Butyl-9,10-dimethoxy-7,7-dimethyl-1,3,4,6,7,11bβ-hexahydro-2H-pyrido[2,1-a]isoquinolin-2β-ylamine hydrochloride,
rac-7β-Butyl-11,12-dimethoxy-2,3,4,4aβ,6,7,8,9,9aα,13bβ-decahydro-1H-pyrido[1,2-f]phenanthridin-8β-ylamine hydrochloride,
rac-7β-Butyl-11,12-dimethoxy-2,3,4,4aβ,6,7,8,9,9aα13bβ-decahydro-1H-pyrido[1,2-f]phenanthridin-8α-ylamine hydrochloride,
rac-3β-Butyl-7α-(3,4-dimethoxy-phenyl)-9,10-dimethoxy-6α-methyl-1,3,4,6,7,11bβ-hexahydro-2H-pyrido[2,1-a]isoquinolin-2-ylamine hydrochloride,
and pharmaceutically acceptable salts thereof.

Further preferred compounds of formula (I) are those selected from the group consisting of:
rac-9,10-dimethoxy-3β-(3-methyl-butyl)-1,3,4,6,7,11bβ-hexahydro-2H-pyrido[2,1-a]isoquinolin-2α-ylamine,
rac-7β-butyl-11,12-dimethoxy-2,3,4,4a,6,7,8,9,9a,13bβ-decahydro-1H-pyrido[1,2-f]phenanthridin-8β-ylamine,
rac-3β-butyl-9,10-dimethoxy-1,3,4,6,7,11bβ-hexahydro-2H-pyrido[2,1-a]isoquinolin-2α-ylamine chlorohydrate (1:2),
rac-7β-butyl-11,12-dimethoxy-2,3,4,4a,6,7,8,9,9a,13bβ-decahydro-1H-pyrido[1,2-f]phenanthridin-8β-ylamine chlorohydrate (1:2),
rac-2α-amino-3β-butyl-10-methoxy-1,3,4,6,7,11bβ-hexahydro-2H-pyrido[2,1-a]isoquinolin-9-ol chlorohydrate (1:2),
rac-2α-amino-3β-butyl-10-methoxy-1,3,4,6,7,11bβ-hexahydro-2H-pyrido[2,1-a]isoquinolin-9-ol, and
rac-9,10-dimethoxy-3β-phenyl-1,3,4,6,7,11bβ-hexahydro-2H-pyrido[2,1-a]isoquinolin-2-ylamine,
and pharmaceutically acceptable salts thereof.

Especially preferred compounds of formula (I) are those selected from the group consisting of:
rac-9,10-dimethoxy-3β-phenyl-1,3,4,6,7,11bβ-hexahydro-2H-pyrido[2,1-a]isoquinolin-2-ylamine,
rac-9,10-Dimethoxy-3α-phenyl-1,3,4,6,7,11bα-hexahydro-2H-pyrido[2,1-a]isoquinolin-2α-ylamine,
rac-9,10-Dimethoxy-3α-phenyl-1,3,4,6,7,11bα-hexahydro-2H-pyrido[2,1-a]isoquinolin-2β-ylamine,
9,10-Dimethoxy-3α-phenyl-1,3,4,6,7,11bα-hexahydro-2H-pyrido[2,1-a]isoquinolin-2α-ylamine,
9,10-Dimethoxy-3α-phenyl-1,3,4,6,7,11bα-hexahydro-2H-pyrido[2,1-a]isoquinolin-2β-ylamine,
9,10-Dimethoxy-3β-phenyl-1,3,4,6,7,11bβ-hexahydro-2H-pyrido[2,1-a]isoquinolin-2β-ylamine, and
9,10-Dimethoxy-3β-phenyl-1,3,4,6,7,11bβ-hexahydro-2H-pyrido[2,1-a]isoquinolin-2α-ylamine,
and pharmaceutically acceptable salts thereof.

Most preferred compounds of formula (I) are those selected from the group consisting of:
9,10-Dimethoxy-3α-phenyl-1,3,4,6,7,11bα-hexahydro-2H-pyrido[2,1-a]isoquinolin-2α-ylamine,
9,10-Dimethoxy-3α-phenyl-1,3,4,6,7,11bα-hexahydro-2H-pyrido[2,1-a]isoquinolin-2β-ylamine,
9,10-Dimethoxy-3β-phenyl-1,3,4,6,7,11bβ-hexahydro-2H-pyrido[2,1-a]isoquinolin-2β-ylamine, and
9,10-Dimethoxy-3β-phenyl-1,3,4,6,7,11bβ-hexahydro-2H-pyrido[2,1-a]isoquinolin-2α-ylamine,
and pharmaceutically acceptable salts thereof.

Compounds of formula (I) can have one or more asymmetric carbon atoms and can exist in the form of optically pure enantiomers or as racemates. The invention embraces all of these forms.

It will be appreciated, that the compounds of formula (I) in this invention may be derivatised at functional groups to provide derivatives which are capable of conversion back to the parent compound in vivo.

The present invention also relates to a process for the manufacture of compounds of formula (I) as defined above, which process comprises reducing an oxime of formula (II)

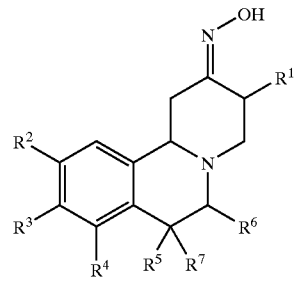

(II)

wherein $R^1$, $R^2$, $R^3$, $R^4$, $R^5$, $R^6$ and $R^7$ are as defined above, optionally followed by conversion into a pharmaceutically acceptable salt thereof.

Hydrogenation of the above oxime of formula II can be performed according to methods known in the art. For example, the reaction can be performed in the presence of a catalyst such as Raney nickel, platin or palladium in an inert solvent, such as ethanol, at a temperature of about 20° C. to 80° C.

Hydroxy groups in the compounds of formula II can be present in a protected form, for example as a benzyl ether. Such protecting groups can be removed according to processes known in the art, e.g. in case of benzyl ether by catalytic hydrogenation.

Oximes of formula II are known in the art or can be prepared starting from ketones of the formula III by methods known in the art and as exemplified or in analogy thereto.

Compounds of formula (III):

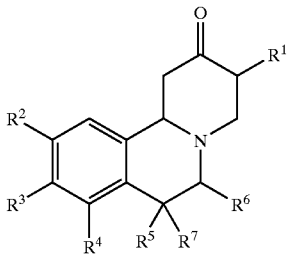

wherein $R^1$, $R^2$, $R^3$, $R^4$, $R^5$, $R^6$ and $R^7$ are as defined above, can be prepared by reacting a compound of the formula (IV):

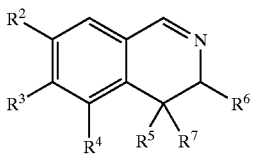

wherein $R^2$, $R^3$, $R^4$, $R^5$, $R^6$ and $R^7$ are as defined above, with a compound of the formula (V):

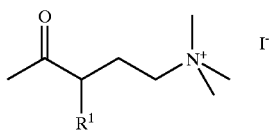

wherein $R^1$ is as defined above, or a compound of the formula (VI):

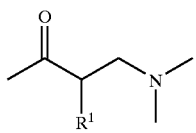

wherein $R^1$ is as defined above.

Compounds of formula (IV) are known in the art or can be prepared by oxidation of compounds of formula (VIII):

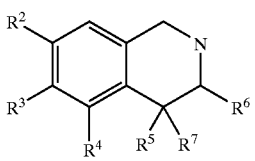

wherein $R^2$, $R^3$, $R^4$, $R^5$, $R^6$ and $R^7$ are as defined above, according to methods known in the art and as exemplified or in analogy thereto.

Alternatively, compounds of formula (VII)

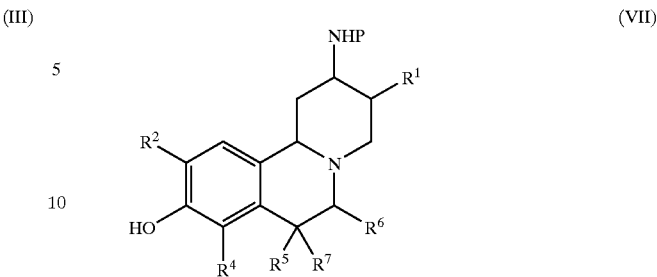

wherein $R^1$, $R^2$, $R^4$, $R^5$, $R^6$ and $R^7$ are as defined above and P represents an amino protecting group;

may be reacted with an alcohol

wherein R is lower alkyl substituted by aryl, heterocyclyl or lower alkoxycarbonyl;

in the presence of triphenylphosphine and di-t-butyl azodicarboxylate, followed by deprotection.

Alternatively, compounds of formula (III) wherein $R^1$ is aryl or heteroaryl may be prepared by reacting a compound of formula (III) wherein $R^2$, $R^3$, $R^4$, $R^5$, $R^6$ and $R^7$ are as defined above and $R^1$ is hydrogen ($R^1$=H) with an aryl halogenide respectively a heteroaryl halogenide

wherein R is aryl or heteroaryl and X is chloride, bromide, iodide or triflate; in the presence of a palladium catalyst like palladium acetate or tetrakis-triphenylphosphine palladium complex, a ligand, like tri-tert-butylphosphine or other phosphines, and a base like sodium tert-butoxide in an inert solvent like tetrahydrofurane at moderate temperature of 20 to 100° C. (in analogy to the methods described in J. M. Fox, X. Huang, A. Chieffi, S. L. Buchwald., J. Am. Chem. Soc. 2000, 122, 1360–1370. and M. Kawatsura and J. F. Hartwig, J. Am. Chem. Soc. 1999, 121, 1473–1478).

Preferred amino protecting groups are t-butyloxycarbonyl (Boc), benzyloxycarbonyl (Z) and 9-fluorenylmethyloxycarbonyl (Fmoc), with t-butyloxycarbonyl (Boc) being especially preferred. Deprotection can be performed by methods known in the art.

The invention further relates to compounds of formula (I) as defined above, when manufactured according to a process as defined above.

As described above, the compounds of formula (I) of the present invention can be used as medicaments for the treatment and/or prophylaxis of diseases which are associated with DPP-IV such as diabetes, particularly non-insulin dependent diabetes mellitus, impaired glucose tolerance, Bowl disease, Colitis Ulcerosa, Morbus Crohn, obesity, and/or metabolic syndrome, preferably non-insulin dependent diabetes mellitus and/or impaired glucose tolerance. Furthermore, the compounds of the present invention can be used as diuretic agents or for the treatment and/or prophylaxis of hypertension.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with DPP-IV such as diabetes, particularly non-insulin dependent diabetes mellitus, impaired glucose tolerance, Bowl disease, Colitis Ulcerosa, Morbus Crohn, obesity, and/or metabolic syndrome, preferably for use as therapeutic active substances for the treatment and/or prophylaxis of non-insulin dependent diabetes mellitus and/or impaired glucose tolerance. Furthermore, the invention relates to compounds as defined above for use as diuretic agents or for use as therapeutic active substances for the treatment and/or prophylaxis of hypertension.

In another embodiment, the invention relates to a method for the treatment and/or prophylaxis of diseases which are associated with DPP-IV such as diabetes, particularly non-insulin dependent diabetes mellitus, impaired glucose tolerance, Bowl disease, Colitis Ulcerosa, Morbus Crohn, obesity, and/or metabolic syndrome, preferably for the treatment and/or prophylaxis of non-insulin dependent diabetes mellitus and/or impaired glucose tolerance, which method comprises administering a compound as defined above to a human being or animal. Furthermore, the invention relates to a method for the treatment and/or prophylaxis as defined above, wherein the disease is hypertension or wherein a diuretic agent has a beneficial effect.

The invention further relates to the use of compounds as defined above for the treatment and/or prophylaxis of diseases which are associated with DPP-IV such as diabetes, particularly non-insulin dependent diabetes mellitus, impaired glucose tolerance, Bowl disease, Colitis Ulcerosa, Morbus Crohn, obesity, and/or metabolic syndrome, preferably for the treatment and/or prophylaxis of non-insulin dependent diabetes mellitus and/or impaired glucose tolerance. Furthermore, the invention relates to the use as defined above, wherein the disease is hypertension or to the use as diuretic agent.

In addition, the invention relates to the use of compounds as defined above for the preparation of medicaments for the treatment and/or prophylaxis of diseases which are associated with DPP-IV such as diabetes, particularly non-insulin dependent diabetes mellitus, impaired glucose tolerance, Bowl disease, Colitis Ulcerosa, Morbus Crohn, obesity, and/or metabolic syndrome, preferably for the treatment and/or prophylaxis of non-insulin dependent diabetes mellitus and/or impaired glucose tolerance. Such medicaments comprise a compound as defined above. Furthermore, the invention relates to the use as defined above, wherein the disease is hypertension or the use for the preparation of diuretic agents.

In context with the methods and uses defined above, the following diseases relate to a preferred embodiment: diabetes, particularly non-insulin dependent diabetes mellitus, impaired glucose tolerance, obesity, and/or metabolic syndrome, preferably non-insulin dependent diabetes mellitus and/or impaired glucose tolerance.

The compounds of formula (I) can be manufactured by the methods given below, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The following tests were carried out in order to determine the activity of the compounds of formula I.

Activity of DPP-IV inhibitors are tested with natural human DPP-IV derived from a human plasma pool or with recombinant human DPP-IV. Human citrate plasma from different donors is pooled, filtered through a 0.2 micron membrane under sterile conditions and aliquots of 1 ml are shock frozen and stored at −120° C. until used. In the calorimetric DPP-IV assay 5 to 10 µl human plasma and in the fluorometric assay 1.0 µl of human plasma in a total assay volume of 100 µl is used as an enzyme source. The cDNA of the human DPP-IV sequence of amino acid 31- to 766, restricted for the N-terminus and the transmembrane domain, is cloned into pichia pastoris. Human DPP-IV is expressed and purified from the culture medium using conventional column chromatography including size exclusion and anion and cation chromatography. The purity of the final enzyme preparation of Coomassie blue SDS-PAGE is>95%. In the calorimetric DPP-IV assay 20 ng rec.-h DPP-IV and in the fluorometric assay 2 ng rec-h DPP-IV in a total assay volume of 100 µl is used as an enzyme source.

In the fluorogenic assay Ala-Pro-7-amido-4-trifluoromethylcoumarin (Calbiochem No 125510) is used as a substrate. A 20 mM stock solution in 10% DMF/H$_2$O is stored at −20° C. until use. In IC$_{50}$ determinations a final substrate concentration of 50 µM is used. In assays to determine kinetic parameters as K$_m$, V$_{max}$, K$_i$, the substrate concentration is varied between 10 µM and 500 µM.

In the colorimetric assay H-Ala-Pro-pNA. HCl (Bachem L-1115) is used as a substrate. A 10 mM stock solution in 10% MeOH/H$_2$O is stored at −20° C. until use. In IC$_{50}$ determinations a final substrate concentration of 200 µM is used. In assays to determine kinetic parameters as K$_m$, V$_{max}$, K$_i$, the substrate concentration is varied between 100 µM and 2000 µM.

Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression.

The absorption of pNA liberated from the calorimetric substrate is detected in a Packard SpectraCount at 405 nM continuously every 2 minutes for 30 to 120 minutes. Initial rate constants are calculated by best fit linear regression.

DPP-IV activity assays are performed in 96 well plates at 37° C. in a total assay volume of 100 µl. The assay buffer consists of 50 mM Tris/HCl pH 7.8 containing 0.1 mg/ml BSA and 100 mM NaCl. Test compounds are solved in 100% DMSO, diluted to the desired concentration in 10% DMSO/H$_2$O. The final DMSO concentration in the assay is 1% (v/v).

At this concentration enzyme inactivation by DMSO is <5%. Compounds are with (10 minutes at 37° C.) and without preincubation with the enzyme. Enzyme reactions are started with substrate application followed by immediate mixing.

IC$_{50}$ determinations of test compounds are calculated by non-linear best fit regression of the DPP-IV inhibition of at least 5 different compound concentrations. Kinetic parameters of the enzyme reaction are calculated at at least 5 different substrate concentrations and at least 5 different test compound concentrations.

The preferred compounds of the present invention exhibit IC$_{50}$ values of 1 nM to 10 µM, more preferably of 1–100 nM, as shown in the following table.

| Example | IC$_{50}$ [µM] |
| --- | --- |
| 5 | 0.57 |
| 17 | 0.14 |

-continued

| Example | IC$_{50}$ [μM] |
|---------|----------------|
| 20 | 0.52 |
| 36 | 0.16 |
| 39 | 0.62 |
| 43b | 0.34 |
| 44 | 0.22 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols. Depending on the nature of the active ingredient no carriers might be required for soft gelatine capsules. In this case, the soft gel capsule is considered a carrier. Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

EXAMPLES

Abbreviations:

MS=mass spectrometry, ISP=ion spray (positive ion) corresponds to ESI (electrospray, positive ion), b.p.=boiling point, m.p.=melting point, aq.=aqueous, r.t.=room temperature.

Example 1 rac-3β-Butyl-9,10-dimethoxy-1,3,4,6,7,11bβ-hexahydro-2H-pyrido[2,1-a]isoquinolin-2β-ylamine and rac-3β-butyl-9,10-dimethoxy-1,3,4,6,7,11bβ-hexahydro-2H-pyrido[2,1-a]isoquinolin-2α-ylamine (i) A solution of 6.8 g of 3,4-dihydro-6,7-dimethoxy-isoquinoline in 70 ml of ethanol is treated with 11.4 g of (2-acetylhexyl)trimethylammonium iodid and heated under reflux for 1.5 hours. The reaction mixture is cooled down and treated with a solution of 6.8 g of potassium hydroxide in 70 ml of water. The ethanol is evaporated and the aq. solution is extracted three times with 80 ml of dichloromethane. The combined organic solutions are dried over anhydrous sodium sulfate and evaporated. The solid red residue is purified by chromatography (silica gel, hexane/ethyl acetate 4:1) and crystallized from isopropyl ether. 7.0 g rac-3β-Butyl-9,10-dimethoxy-1,3,4,6,7,11bβ-hexahydro-pyrido[2,1-a]isoquinolin-2-one are obtained, m.p.=117° C.

(ii) A solution of 5.5 g hydroxylamine hydrochloride in 50 ml of water and 20 ml of ethanol is made alkaline (pH 9) with 7.27 ml of N sodium hydroxide solution and a solution of 3.35 g rac-3β-butyl-9,10-dimethoxy-1,3,4,6,7,11bβ-hexahydro-pyrido[2,1-a]isoquinolin-2-one in 50 ml of ethanol is added. The reaction mixture is stirred for 45 minutes at 45° C., half concentrated and then cooled to 0° C. The precipitated product is filtered and washed with ethanol/water (1:1), subsequently with water. 3.26 g rac-3β-butyl-9,10-dimethoxy-1,3,4,6,7,11bβ-hexahydro-pyrido[2,1-a]isoquinolin-2-one oxime are obtained, m.p.=143–145° C.

(iii) A suspension of 1.5 g rac-3β-butyl-9,10-dimethoxy-1,3,4,6,7,11bβ-hexahydro-pyrido[2,1-a]isoquinolin-2-one oxime in 40 ml of ethanol and 40 ml of water is treated with 1.25 g of a nickel-aluminum alloy and 4.935 ml of an aq. 32% sodium hydroxide solution are added dropwise. The mixture is stirred thoroughly for four hours at room temperature, then filtered and washed with ethanol/water (1:1). The filtrate is extracted twice with dichloro-methane and the combined organic solutions are washed with a saturated solution of sodium chloride, dried over anhydrous sodium sulfate and evaporated. The solid residue is purified by chromatography (silica gel, dichloromethane-methanol/25% ammonium hydroxide (0–16%)). There are obtained (a) 0.38 g rac-3β-butyl-9,10-dimethoxy-1,3,4,6,7,11bβ-hexahydro-2H-pyrido[2,1-a]isoquinolin-2β-ylamine as a resin, MS (ISP) 319.4 (M+H)$^+$ and (b) 0.45 g rac-3β-butyl-9,10-dimethoxy-1,3,4,6,7,11bβ-hexahydro-2H-pyrido[2,1-a]isoquinolin-2α-ylamine as a resin, MS (ISP) 319.4 (M+H)$^+$.

Examples 2–18

The following compounds are prepared in analogy to Example 1:

2. rac-9,10-Dimethoxy-3β-propyl-1,3,4,6,7,11bβ-hexahydro-2H-pyrido[2,1-a]isoquinolin-2β-ylamine as a resin, MS (ISP) 305.3 (M+H)$^+$.

3. rac-9,10-Dimethoxy-3β-propyl-1,3,4,6,7,11bβ-hexahydro-2H-pyrido[2,1-a]isoquinolin-2α-ylamine as a resin, MS (ISP) 305.3 (M+H)+.
4. rac-9,10-Dimethoxy-3β-(3-methyl-butyl)-1,3,4,6,7,11bβ-hexahydro-2H-pyrido[2,1-a]isoquinolin-2β-ylamine as a resin, MS (ISP) 333.3 (M+H)+.
5. rac-9,10-Dimethoxy-3β-(3-methyl-butyl)-1,3,4,6,7,11bβ-hexahydro-2H-pyrido[2,1-a]isoquinolin-2α-ylamine as a resin, MS (ISP) 333.3 (M+H)+.
6. rac-3β-(2-Ethyl-butyl)-9,10-dimethoxy-1,3,4,6,7,11bβ-hexahydro-2H-pyrido[2,1-a]isoquinolin-2β-ylamine as a resin, MS (ISP) 347.5 (M+H)+.
7. rac-3β-(2-Ethyl-butyl)-9,10-dimethoxy-1,3,4,6,7,11bβ-hexahydro-2H-pyrido[2,1-a]isoquinolin-2α-ylamine as a resin, MS (ISP) 347.5 (M+H)+.
8. rac-3β-Cyclopropylmethyl-9,10-dimethoxy-1,3,4,6,7,11bβ-hexahydro-2H-pyrido[2,1-a]isoquinolin-2β-ylamine as a resin, MS (ISP) 317.3 (M+H)+.
9. rac-3β-Cyclopropylmethyl-9,10-dimethoxy-1,3,4,6,7,11bβ-hexahydro-2H-pyrido[2,1-a]isoquinolin-2α-ylamine as a resin, MS (ISP) 317.3 (M+H)+.
10. rac-3β-Butyl-9-methoxy-1,3,4,6,7,11bβ-hexahydro-2H-pyrido[2β-a]isoquinolin-2α-ylamine as a resin, MS (ISP) 347.5 (M+H)+.
11. rac-3β-Butyl-1,3,4,6,7,11bβ-hexahydro-2H-pyrido[2,1-a]isoquinolin-2β-ylamine as an oil, MS (ISP) 359.2 (M+H)+.
12. rac-3β-Butyl-1,3,4,6,7,11bβ-hexahydro-2H-pyrido[2,1-a]isoquinolin-2α-ylamine as an oil, MS (ISP) 359.2 (M+H)+.
13. rac-3β-Butyl-8,9-dimethoxy-1,3,4,6,7,11bβ-hexahydro-2H-pyrido[2,1-a]isoquinolin-2β-ylamine as a resin, MS (ISP) 319.5 (M+H)+.
14. rac-3β-Butyl-8,9-dimethoxy-1,3,4,6,7,11bβ-hexahydro-2H-pyrido[2,1-a]isoquinolin-2α-ylamine, MS (ISP) 319.5 (M+H)+.
15. rac-2β-Amino-3β-butyl-9-methoxy-1,3,4,6,7,11bβ-hexahydro-2H-pyrido[2,1-a]isoquinolin-10-ol as an oil, MS (ISP) 305.3 (M+H)+.
16. rac-2α-Amino-3β-butyl-9-methoxy-1,3,4,6,7,11bβ-hexahydro-2H-pyrido[2,1-a]isoquinolin-10-ol, MS (ISP) 305.3 (M+H)+.
17. rac-7β-Butyl-11,12-dimethoxy-2,3,4,4a,6,7,8,9,9a,13bβ-decahydro-1H-pyrido[1,2-f]phenanthridin-8β-ylamine as a solid, MS (ISP) 373.5 (M+H)+.
18. rac-7β-Butyl-11,12-dimethoxy-2,3,4,4a,6,7,8,9,9a,13bβ-decahydro-1H-pyrido[1,2-f]phenanthridin-8α-ylamine as an oil, MS (ISP) 373.5 (M+H)+.

The educts used in Examples 1–18 (compounds of formulae II and III) which have not been described before can be prepared according to the procedures described below or in analogy thereto.

Oxime Derivatives (Compounds of Formula II)

The following compounds are prepared in analogy to the procedure used for the preparation of rac-3β-butyl-9,10-dimethoxy-1,3,4,6,7,11bβ-hexahydro-pyrido[2,1-a]isoquinolin-2-one oxime described above in Example 1:
rac-9,10-Dimethoxy-3-β-(3-methyl-butyl)-1,3,4,6,7,11bβ-hexahydro-pyrido[2,1-a]isoquinolin-2-one oxime, MS (ISP): 347.4 (M+H)+.
rac-3β-(2-Ethyl-butyl)-9,10-dimethoxy-1,3,4,6,7,11bβ-hexahydro-pyrido[2,1-a]isoquinolin-2-one oxime, MS (ISP): 361.3 (M+H)+.
rac-3β-Cyclopropylmethyl-9,10-dimethoxy-1,3,4,6,7,11bβ-hexahydro-pyrido[2,1-a]isoquinolin-2-one oxime, m.p.=156–158° C.
rac-3β-Butyl-9-methoxy-1,3,4,6,7,11bβ-hexahydro-pyrido[2,1-a]isoquinolin-2-one oxime, m.p.=155–159° C.
rac-7β-Butyl-1,3,4,6,7,13bβ-hexahydro-pyrido[1,2-a]isoquinolin-2-one oxime, m.p.=140–144° C.
rac-3β-Butyl-8,9-dimethoxy-1,3,4,6,7,11bβ-hexahydro-pyrido[2,1-a]isoquinolin-2-one oxime, m.p.=148–150° C.
rac-3β-Butyl-10-hydroxy-9-methoxy-1,3,4,6,7,11bβ-hexahydro-pyrido[2,1-a]isoquinolin-2-one oxime, m.p.=118–120° C.
rac-7-Butyl-11,12-dimethoxy-1,2,3,4,4a,6,7,9,9a,13b-decahydro-pyrido[1,2-f]phenanthridin-8-one oxime, m.p.=122–125° C.

Ketone Derivatives (Compounds of Formula III)

The following compounds are prepared in analogy to the procedure used for the preparation of rac-3β-butyl-9,10-dimethoxy-1,3,4,6,7,11bβ-hexahydro-pyrido[2,1-a]isoquinolin-2-one described above in Example 1:
rac-3β-Butyl-1,3,4,6,7,11bβ-hexahydro-pyrido[2,1-a]isoquinolin-2-one, m.p.=95° C.
rac-3β-Butyl-8,9-dimethoxy-1,3,4,6,7,11bβ-hexahydro-pyrido[2,1-a]isoquinolin-2-one, m.p.=89–91° C.
rac-3β-Butyl-10-hydroxy-9-methoxy-1,3,4,6,7,11bβ-hexahydro-pyrido[2,1-a]isoquinolin-2-one, m.p.=136° C.
rac-7β-Butyl-11,12-dimethoxy-2,3,4,4a,6,7,8,9,9a,13bβ-decahydro-1H-pyrido[1,2-f]phenanthridin-8-one, m.p.=157° C.
rac-3β-Cyclopropylmethyl-9,10-dimethoxy-1,3,4,6,7,11bβ-hexahydro-pyrido[2,1-a]isoquinolin-2-one.

To a solution of 3 g of 3,4-dihydro-6,7-dimethoxy-isoquinoline in 10 ml of ethanol is added 2.45 g of 3-[(dimethylamino)methyl]-4-cyclopropyl-2-butanone and the mixture is stirred for 18 hours at room temperature. The solids are filtered off, washed with water and re-crystallized from hexane. 2.6 g rac-3β-Cyclopropylmethyl-9,10-dimethoxy-1,3,4,6,7,11bβ-hexahydro-pyrido[2,1-a]isoquinolin-2-one are obtained, m.p.=99–101° C.

The educt used above, rac-3-cyclopropylmethyl-4-dimethylamino-butan-2-one (compound of formula VI), can be prepared by the procedure described below or in analogy thereto.

(i) 36.2 g of ethyl 3-oxo-butyrate are added dropwise with stirring at room temperature to a solution of 7 g of sodium in 160 ml of ethanol. Thereafter, 45.1 g of (bromomethyl)-cyclopropan are added and the mixture is heated under reflux for two hours. The reaction mixture is allowed to cool down to room temperature, then it is poured on 500 ml of water and extracted three times with diethylether. After drying on anhydrous sodium sulfate the solvent is evaporated and the residue is distilled. 38.9 g of ethyl 2-acetyl-cyclopropylpropionate are obtained, b.p.=35–36° C./0.3 mbar.

(ii) A solution of 3.9 g of potassium hydroxide in 30 ml of water is added at room temperature to a solution of 11.6 g of ethyl 2-acetyl-cyclopropylpropionate. After stirring for four hours at room temperature the mixture is neutralized with approx. 5.2 ml of concentrated hydrochloric acid and subsequently 5.16 g of dimethylamine-hydrochloride and 4.82 ml of 36.5% formaldehyde-solution are added. Thereafter 5.24 ml of concentrated hydrochloric acid are added within one hour with stirring at room temperature and the mixture is stirred for 18 hours at the same temperature and extracted twice with diethylether. After drying on anhydrous sodium sulfate the solvent is evaporated. The residue is purified by chromatography (silica gel, dichloromethane-methanol/25% ammonium hydroxide (0–10%)) and subsequently distilled (Kugelrohr). 2.9 g of rac-3- cyclopropylmethyl-4-dimethylamino-butan-2-one are obtained, b.p.=95° C./11 mbar.

Example 19

To a solution of 380 mg of rac-3β-butyl-9,10-dimethoxy-1,3,4,6,7,11bβ-hexahydro-2H-pyrido[2,1-a]isoquinolin-2β-ylamine in 40 ml of ethanol is added 2 ml of a saturated solution of hydrochloric acid in ethanol. The mixture is stirred for one hour at room temperature and the solids are filtered off. 381 mg of rac-3β-butyl-9,10-dimethoxy-1,3,4,6,7,11bβ-hexahydro-2H-pyrido[2,1-a]isoquinolin-2β-ylamine chlorohydrate (1:2) are obtained, MS (ISP) 319.5 (M+H)+.

Examples 20–42

The following compounds are prepared in analogy to Example 19:

20. rac-3β-Butyl-9,10-dimethoxy-1,3,4,6,7,11bβ-hexahydro-2H-pyrido[2,1-a]isoquinolin-2α-ylamine chlorohydrate (1:2), MS (ISP) 319.5 (M+H)+.
21. rac-9,10-Dimethoxy-3β-propyl-1,3,4,6,7,11bβ-hexahydro-2H-pyrido[2,1-a]isoquinolin-2β-ylamine chlorohydrate (1:2), m.p.=282–288° C., MS (ISP) 305.4 (M+H)+.
22. rac-9,10-Dimethoxy-3β-propyl-1,3,4,6,7,11bβ-hexahydro-2H-pyrido[2,1-a]isoquinolin-2α-ylamine chlorohydrate (1:2), m.p.=270–275° C. dec., MS (ISP) 305.3 (M+H)+.
23. rac-9,10-Dimethoxy-3β-(3-methyl-butyl)-1,3,4,6,7,11bβ-hexahydro-2H-pyrido[2,1-a]isoquinolin-2β-ylamine chlorohydrate (1:2) as a solid, MS (ISP) 333.3 (M+H)+.
24. rac-9,10-Dimethoxy-3β-(3-methyl-butyl)-1,3,4,6,7,11bβ-hexahydro-2H-pyrido[2,1-a]isoquinolin-2α-ylamine chlorohydrate (1:2) as a solid, MS (ISP) 333.4 (M+H)+.
25. rac-3β-(2-Ethyl-butyl)-9,10-dimethoxy-1,3,4,6,7,11bβ-hexahydro-2H-pyrido[2,1-a]isoquinolin-2β-ylamine chlorohydrate (1:2) as a solid, MS (ISP) 347.5 (M+H)+.
26. rac-3β-(2-Ethyl-butyl)-9,10-dimethoxy-1,3,4,6,7,11bβ-hexahydro-2H-pyrido[2,1-a]isoquinolin-2α-ylamine chlorohydrate (1:2) as a solid, MS (ISP) 347.4 (M+H)+.
27. rac-3β-Cyclopropylmethyl-9,10-dimethoxy-1,3,4,6,7,11bβ-hexahydro-2H-pyrido[2,1-a]isoquinolin-2β-ylamine chlorohydrate (1:2) as a solid, MS (ISP) 317.3 (M+H)+.
28. rac-3β-Cyclopropylmethyl-9,10-dimethoxy-1,3,4,6,7,11bβ-hexahydro-2H-pyrido[2,1-a]isoquinolin-2α-ylamine chlorohydrate (1:2), m.p.=197–210° C., MS (ISP) 317.3 (M+H)+.
29. rac-3β-Butyl-9-methoxy-1,3,4,6,7,11bβ-hexahydro-2H-pyrido[2,1-a]isoquinolin-2α-ylamine chlorohydrate (1:2), m.p.=197–210° C., MS (ISP) 289.3 (M+H)+.
30. rac-3β-Butyl-1,3,4,6,7,11bβ-hexahydro-2H-pyrido[2,1-a]isoquinolin-2β-ylamine chlorohydrate (1:2) as a solid, MS (ISP) 259.3 (M+H)+.
31. rac-3β-Butyl-1,3,4,6,7,11bβ-hexahydro-2H-pyrido[2,1-a]isoquinolin-2α-ylamine chlorohydrate (1:2) as a solid, MS (ISP) 259.2 (M+H)+.
32. rac-3β-Butyl-8,9-dimethoxy-1,3,4,6,7,11bβ-hexahydro-2H-pyrido[2,1-a]isoquinolin-2β-ylamine chlorohydrate (1:2), m.p.=116–120° C., MS (ISP) 319.5 (M+H)+.
33. rac-3β-Butyl-8,9-dimethoxy-1,3,4,6,7,11bβ-hexahydro-2H-pyrido[2,1-a]isoquinolin-2α-ylamine chlorohydrate (1:2), m.p.=260–265° C., MS (ISP) 319.5 (M+H)+.
34. rac-2β-Amino-3β-butyl-9-methoxy-1,3,4,6,7,11bβ-hexahydro-2H-pyrido[2,1-a]isoquinolin-10-ol chlorohydrate (1:2), m.p.=295–299° C., MS (ISP) 305.4 (M+H)+.
35. rac-2α-Amino-3β-butyl-9-methoxy-1,3,4,6,7,11bβ-hexahydro-2H-pyrido[2,1-a]isoquinolin-10-ol chlorohydrate (1:2), m.p.=322–324° C., MS (ISP) 305.4 (M+H)+.
36. rac-7β-Butyl-11,12-dimethoxy-2,3,4,4a,6,7,8,9,9a,13bβ-decahydro-1H-pyrido[1,2-f]phenanthridin-8β-ylamine chlorohydrate (1:2), m.p.=225–233° C., MS (ISP) 373.4 (M+H)+.
37. rac-7β-Butyl-11,12-dimethoxy-2,3,4,4a,6,7,8,9,9a,13bβ-decahydro-1H-pyrido[1,2-f]phenanthridin-8α-ylamine chlorohydrate (1:2), m.p.=215–222° C., MS (ISP) 373.5 (M+H)+.
38. rac-2β-Amino-3β-butyl-10-methoxy-1,3,4,6,7,11bβ-hexahydro-2H-pyrido[2,1-a]isoquinolin-9-ol chlorohydrate (1:2), m.p.=230–237° C., MS (ISP) 305.5 (M+H)+.
39. rac-2α-Amino-3β-butyl-10-methoxy-1,3,4,6,7,11bβ-hexahydro-2H-pyrido[2,1-a]isoquinolin-9-ol chlorohydrate (1:2), m.p.=230–250° C., MS (ISP) 305.5 (M+H)+.
40. rac-3β-Butyl-9-methoxy-1,3,4,6,7,11bβ-hexahydro-2H-pyrido[2,1-a]isoquinolin-2β-ylamine chlorohydrate (1:2), MS (ISP) 289.3 (M+H)+.
41. rac-3β-Isobutyl-9,10-dimethoxy-1,3,4,6,7,11bβ-hexahydro-2H-pyrido[2,1-a]isoquinolin-2β-ylamine chlorohydrate (1:2), MS (ISP) 319.4 (M+H)+.
42. rac-3β-Isobutyl-9,10-dimethoxy-1,3,4,6,7,11bβ-hexahydro-2H-pyrido[2,1-a]isoquinolin-2α-ylamine chlorohydrate (1:2), MS (ISP) 319.4 (M+H)+.

Example 43

A solution of 500 mg of rac-9-benzyloxy-3β-butyl-10-methoxy-1,3,4,6,7,11bβ-hexahydro-pyrido[2,1-a]isoquinolin-2-one oxime in 60 ml of ethanol is treated with 1 g of a nickel-aluminum alloy and stirred thoroughly for 18 hours at room temperature. The catalyst is filtered off, washed with ethanol/water (1:1) and the filtrate is evaporated. The residue is purified by chromatography (silica gel, dichloromethane-methanol/25% ammonium hydroxide (0–12%)). There were obtained (a) 0.08 g of rac-2β-amino-3β-butyl-10-methoxy-1,3,4,6,7,11bβ-hexahydro-2H-pyrido[2,1-a]isoquinolin-9-ol as a solid, MS (ISP) 305.4 (M+H)+ and (b) 0.24 g of rac-2α-amino-3β-butyl-10-methoxy-1,3,4,6,7,11bβ-hexahydro-2H-pyrido[2,1-a]isoquinolin-9-ol as a solid, MS (ISP) 305.4 (M+H)+.

The educts used in Example 43 are prepared in analogy to the preparation of rac-3β-butyl-9,10-dimethoxy-1,3,4,6,7,11b-hexahydro-pyrido[2,1-a]isoquinolin-2-one oxime and rac-3β-butyl-9,10-dimethoxy-1,3,4,6,7,11bβ-hexahydro-pyrido[2,1-a]isoquinolin-2-one as described in Example 1:
rac-9-Benzyloxy-3β-butyl-10-methoxy-1,3,4,6,7,11bβ-hexahydro-pyrido[2,1-a]isoquinolin-2-one oxime, m.p.=148–149° C.
rac-9-Benzyloxy-3β-butyl-10-methoxy-1,3,4,6,7,11bβ-hexahydro-pyrido[2,1-a]isoquinolin-2-one, m.p.=118–119° C.

Examples 44 and 45

The following compounds were prepared in analogy to Example 1:
44. rac-9,10-Dimethoxy-3β-phenyl-1,3,4,6,7,11bβ-hexahydro-2H-pyrido[2,1-a]isoquinolin-2-ylamine, MS (ISP) 339.4 (M+H)+.
45. rac-2α-Amino-3β-butyl-9-methoxy-1,3,4,6,7,11bβ-hexahydro-2H-pyrido[2,1-a]isoquinolin-8-ol as a resin, MS (ISP) 305.4 (M+H)+.

The educts used in Examples 44 and 45 (compounds of formulae II and III) which have not been described above can be prepared according to the procedures described below or in analogy thereto.

Oxime Derivatives (Compounds of Formula II)

The following compound is prepared in analogy to the procedure for the preparation of rac-3β-Butyl-9,10-dimethoxy-1,3,4,6,7,11bβ-hexahydro-pyrido[2,1-a]isoquinolin-2-one oxime described in above Example 1:

rac-9,10-Dimethoxy-3β-phenyl-1,3,4,6,7,11bβ-hexahydro-pyrido[2,1-a]isoquinolin-2-one oxime, m.p.=232–234° C.

Ketone Derivatives (Compounds of Formula III)

The following compounds are prepared in analogy to the procedure for the preparation of rac-3β-Butyl-9,10-dimethoxy-1,3,4,6,7,11bβ-hexahydro-pyrido[2,1-a]isoquinolin-2-one described in above Example 1:

rac-9,10-Dimethoxy-3β-phenyl-1,3,4,6,7,11bβ-hexahydro-pyrido[2,1-a]isoquinolin-2-one, m.p.=232–234° C.
3β-Butyl-8-hydroxy-9-methoxy-1,3,4,6,7,11bβ-hexahydro-pyrido[2,1-a]isoquinolin-2-one, m.p.=232–234° C.

Example 46

A mixture of 4.82 g of rac-3β-butyl-9-methoxy-1,3,4,6,7,11bβ-hexahydro-2H-pyrido[2,1-a]isoquinolin-2α-ylamine in 23 ml of an aq. 48% solution of HBr is stirred 7 h under reflux. The mixture is cooled to 0° C. and an aq. 20% solution of NH$_4$OH is added to reach a pH=9 followed by NaCl till saturation. The product is extracted with dichloromethane. The combined organic layers are dried (Na$_2$SO$_4$) and the solvent is evaporated to obtain 4.80 g of rac-2α-amino-3β-butyl-1,3,4,6,7,11bβ-hexahydro-2H-pyrido[2,1-a]isoquinolin-9-ol as a solid, MS (ISP) 275.4 (M+H)$^+$.

Example 47 rac-3β-Butyl-9-phenethyloxy-1,3,4,6,7,11bβ-hexahydro-2H-pyrido[2,1-a]isoquinolin-2α-ylamine chlorohydrate (1:2)

(i) To a solution of 4.50 g of rac-2α-amino-3β-butyl-1,3,4,6,7,11bβ-hexahydro-2H-pyrido[2,1-a]isoquinolin-9-ol in 36 ml of anhydrous DMF are added Et$_3$N (12.78 ml) and di-t-butyl dicarbonate (4.44 g). After 3 h stirring water (180 ml) is added and the product is extracted with 3 portions of ether. The combined organic layers are dried (Na$_2$SO$_4$) and the solvent is evaporated to obtain the crude product that is purified by chromatography (silica gel, hexane/ethyl acetate 3:1 to pure ethyl acetate). 3.92 g of rac-(3β-butyl-9-hydroxy-1,3,4,6,7,11bβ-hexahydro-2H-pyrido[2,1-a]isoquinolin-2α-yl)-carbamic acid tert-butyl ester are obtained as a solid, m.p.=105° C.

(ii) A mixture of 100 mg of rac-(3β-butyl-9-hydroxy-1,3,4,6,7,11bβ-hexahydro-2H-pyrido[2,1-a]isoquinolin-2α-yl)-carbamic acid tert-butyl ester, phenethyl alcohol (35 μl) and triphenylphosphine on a polystyrene resin (222 mg, ~3 mmol triphenyl-phosphine/g resin) in dichloromethane (2.6 ml) is prepared and di-t-butyl azodicarboxylate is added. The mixture is shaken 18 h, then the polymer is filtered away and washed with dichloromethane and trifluoroacetic acid (2 ml) is added. After 2 h stirring the acid is neutralised by addition of sat. aq. Na$_2$CO$_3$ solution. The organic layer is dried (MgSO$_4$) and the solvent evaporated. The product is isolated as its dihydrochloride by precipitation from a 1.5 M HCl solution in ethyl acetate. 83 mg of rac-3β-butyl-9-phenethyloxy-1,3,4,6,7,11bβ-hexahydro-2H-pyrido[2,1-a]isoquinolin-2α-ylamine chlorohydrate (1:2) are obtained as a solid, MS (IPS) 379.3 (M+H)$^+$.

Examples 48–59

The following compounds can be prepared in analogy to example 47:

48. rac-3β-Butyl-9-ethoxy-1,3,4,6,7,11bβ-hexahydro-2H-pyrido[2,1-a]isoquinolin-2α-ylamine chlorohydrate (1:2) as a solid, MS (ISP) 303.4 (M+H)$^+$.
49. rac-3β-Butyl-9-propoxy-1,3,4,6,7,11bβ-hexahydro-2H-pyrido[2,1-a]isoquinolin-2α-ylamine chlorohydrate (1:2) as a solid, MS (ISP) 317.4 (M+H)$^+$.
50. rac-9-Butoxy-3β-butyl-1,3,4,6,7,11bβ-hexahydro-2H-pyrido[2,1-a]isoquinolin-2α-ylamine dihyrochloride as a solid, MS (ISP) 331.4 (M+H)$^+$.
51. rac-3β-Butyl-9-isobutoxy-1,3,4,6,7,11bβ-hexahydro-2H-pyrido[2,1-a]isoquinolin-2α-ylamine chlorohydrate (1:2) as a solid, MS (ISP) 331.4 (M+H)$^+$.
52. rac-9-Benzyloxy-3β-butyl-1,3,4,6,7,11bβ-hexahydro-2H-pyrido[2,1-a]isoquinolin-2α-ylamine chlorohydrate (1:2) as a solid, MS (ISP) 365.4 (M+H)$^+$.
53. rac-3β-Butyl-9-[2-(4-dimethylamino-phenyl)-ethoxy]-1,3,4,6,7,11bβ-hexahydro-2H-pyrido[2,1-a]isoquinolin-2α-ylamine chlorohydrate (1:2) as a solid, MS (ISP) 422.5 (M+H)$^+$.
54. rac-4-[2-(2α-Amino-3β-butyl-1,3,4,6,7,11bβ-hexahydro-2H-pyrido[2,1-a]isoquinolin-9-yloxy)-ethyl]-benzonitrile chlorohydrate (1:2) as a solid, MS (ISP) 404.6 (M+H)$^+$.
55. rac-3β-Butyl-9-[2-(4-methyl-thiazol-5-yl)-ethoxy]-1,3,4,6,7,11bβ-hexahydro-2H-pyrido[2,1-a]isoquinolin-2α-ylamine chlorohydrate (1:2) as a solid, MS (ISP) 400.6 (M+H)$^+$.
56. rac-3β-Butyl-9-(pyridin-3-ylmethoxy)-1,3,4,6,7,11bβ-hexahydro-2H-pyrido[2,1-a]isoquinolin-2α-ylamine chlorohydrate (1:2) as a solid, MS (ISP) 366.4 (M+H)$^+$.
57. rac-3β-Butyl-9-(pyridin-2-ylmethoxy)-1,3,4,6,7,11bβ-hexahydro-2H-pyrido[2,1-a]isoquinolin-2α-ylamine trihydrochloride as a solid, MS (ISP) 366.3 (M+H)$^+$.
58. rac-(2α-Amino-3β-butyl-1,3,4,6,7,11bβ-hexahydro-2H-pyrido[2,1-a]isoquinolin-9-yloxy)-acetic acid ethyl ester chlorohydrate (1:2) as a solid, MS (ISP) 361.4 (M+H)$^+$.
59. rac-3β-Butyl-9-(2-morpholin-4-yl-ethoxy)-1,3,4,6,7,11bβ-hexahydro-2H-pyrido[2,1-a]isoquinolin-2α-ylamine chlorohydrate (1:2) as a solid, MS (ISP) 388.4 (M+H)$^+$.

Example 60 rac-9,10-Dimethoxy-3β-pyrrol-1-yl-1,3,4,6,7,11bβ-hexahydro-2H-pyrido[2,1-a]isoquinolin-2α-ylamine (i) 2-Amino-9,10-dimethoxy-1,6,7,11b-tetrahydro-4H-pyrido[2,1-a]isoquinoline-3-carboxylic acid ethyl ester A solution of 3-(1-ethoxycarbonylmethyl-6,7-dimethoxy-3,4-dihydro-1H-isoquinolin-2-yl)-propionic acid ethyl ester (Helv. Chim. Acta 1958, 41, 119; 17.1 g, 45.0 mmol) in cyclohexane (340 mL) was treated with sodium ethylate (9.67 g, 135 mmol) and heated in an oil bath, and the ethanol formed during the reaction was removed by distillation over 30 min, while more cyclohexane was added in order to keep the reaction volume constant. After cooling the reaction mixture was neutralized with acetic acid and concentrated. The residue was dissolved in dichloromethane/water 1:1 and brought to pH 10 with concentrated ammonium hydroxide solution. The organic layer was separated, dried (MgSO$_4$), and evaporated. The residue was dissolved in methanol (270 mL) and ammonium acetate (42.3 g, 548 mmol) was added.

After stirring at r.t. for 90 min, the reaction mixture was evaporated and the residue partitioned between dichloromethane and 1 M aq. sodium hydroxide solution. The organic layer was dried (MgSO$_4$), evaporated, and chromatographed (SiO$_2$, CH$_2$Cl$_2$/MeOH/NH$_4$OH 97.5:2.5:0.25) to afford the title compound (9.90 g, 66%). Light yellow solid, MS (ISP) 333.2 (M+H)$^+$.

(ii) rac-3α-tert-Butoxycarbonylamino-9,10-dimethoxy-1,3,4,6,7,11bβ-hexahydro-2H-pyrido[2,1-a]isoquinoline-2β-carboxylic acid ethyl ester Trifluoroacetic acid (18 mL) was added at 0° C. to a solution of 2-amino-9,10-dimethoxy-1,6,7,11b-tetrahydro-4H-pyrido[2,1-a]isoquinoline-3-carboxylic acid ethyl ester (1.00 g, 3.01 mmol) in tetrahydrofuran (9 mL), then after 30 min the homogeneous solution was treated with sodium borohydride (237 mg, 6.02 mmol) and stirred for another 45 min. The reaction mixture was poured onto 2 M aq. sodium hydroxide solution and extracted with dichloromethane. The organic layer was dried (MgSO$_4$) and evaporated. The residue was dissolved in dichloromethane (10 mL), di-tert-butyl-dicarbonate (711 mg, 319 mmol) was added, the solution was stirred at r.t. for 16 h, then evaporated. Chromatography of the residue (SiO$_2$, CH$_2$Cl$_2$/MeOH/NH$_4$OH 97.5:2.5:0.25) produced the title compound (1.14 g, 87%). Light yellow solid, MS (ISP) 435.4 (M+H)$^+$.

(iii) rac-(2α-tert-Butoxycarbonylamino-9,10-dimethoxy-1,3,4,6,7,11bβ-hexahydro-2H-pyrido[2,1-a]isoquinolin-3β-yl)-carbamic acid benzyl ester A solution of rac-2α-tert-butoxycarbonylamino-9,10-dimethoxy-1,3,4,6,7,11bβ-hexahydro-2H-pyrido[2,1-a]isoquinoline-3β-carboxylic acid ethyl ester (1.00 g, 2.30 mmol) in tetrahydrofuran (10 mL) was treated with 1 M aq. sodium hydroxide solution (2.30 mL, 2.30 mmol), and the resultant mixture was stirred at r.t. After 16 h, another portion of 1 M aq. sodium hydroxide solution (0.23 mL, 0.23 mmol) was added, and stirring was continued for 4 h. The solvent was then evaporated, the residue was suspended twice in toluene (50 mL) and concentrated to remove residual water azeotropically. The residue was suspended in toluene (20 mL) and treated with diphenylphosphoryl azide (669 mg, 2.30 mmol) and triethylamine (234 mg, 2.30 mmol). The reaction mixture was stirred at r.t. for 30 min, then heated at 80° C. for 45 min, then benzyl alcohol (374 mg, 3.47 mmol) was added, and the reaction mixture was heated at 100° C. for 72 h. After cooling and partitioning between dichloromethane and water, the organic layer was washed with brine, dried (MgSO$_4$), and evaporated. Chromatography of the residue (SiO$_2$, CH$_2$Cl$_2$/MeOH/NH$_4$OH 95:5:0.25) produced the title compound (278 mg, 24%). White solid, MS (ISP) 512.5 (M+H)$^+$.

(iv) rac-(3b-Amino-9,10-dimethoxy-1,3,4,6,7,11bβ-hexahydro-2H-pyrido[2,1-a]isoquinolin-2α-yl)-carbamic acid tert-butyl ester A solution of rac-(2α-tert-butoxycarbonylamino-9,10-dimethoxy-1,3,4,6,7,11bβ-hexahydro-2H-pyrido[2,1-a]isoquinolin-3β-yl)-carbamic acid benzyl ester (275 mg, 0.538 mmol) in acetic acid (10 mL) was hydrogenated at r.t. and atmospheric pressure in the presence of palladium (10% on activated charcoal, 15 mg). After 30 min, the solvent was evaporated, the residue was treated with toluene (20 mL), the suspension concentrated and the residue dried in vacuo to afford the title compound (247 mg, ca. 85% purity), which was directly used in the next step. Light yellow solid, MS (ISP) 378.4 (M+H)$^+$.

(v) rac-(9,10-Dimethoxy-3β-pyrrol-1-yl-1,3,4,6,7,11bβ-hexahydro-2H-pyrido[2,1-a]isoquinolin-2α-yl)-carbamic acid tert-butyl ester 2,5-dimethoxytetrahydrofuran (41 mg, 0.30 mmol) was added to a solution of rac-(3β-amino-9,10-dimethoxy-1,3,4,6,7,11bβ-hexahydro-2H-pyrido[2,1-a]isoquinolin-2α-yl)-carbamic acid tert-butyl ester (120 mg, 0.27 mmol/85% purity) in acetic acid (1.2 mL, 21 mmol) and pyridine (0.76 mL, 9.5 mmol). The homogeneous solution was heated at 100° C. for 105 min, then evaporated, and the residue was chromatographed (SiO$_2$, heptane/ethyl acetate gradient) to afford the title compound (87 mg, 75%). White solid, MS (ISP) 428.3 (M+H)$^+$.

(vi) rac-9,10-Dimethoxy-3β-pyrrol-1-yl-1,3,4,6,7,11bβ-hexahydro-2H-pyrido[2,1-a]isoquinolin-2α-ylamine rac-(9,10-Dimethoxy-3β-pyrrol-1-yl-1,3,4,6,7,11bβ-hexahydro-2H-pyrido[2,1-a]isoquinolin-2α-yl)-carbamic acid tert-butyl ester (86 mg, 0.20 mmol) was dissolved in hydrogen chloride solution (4 M in dioxane, 1 mL), stirred at r.t. for 1 h, and evaporated. Chromatography of the residue (SiO$_2$, CH$_2$Cl$_2$/MeOH/NH$_4$OH 95:5:0.25) produced the title compound (58 mg, 88%). White solid, MS (ISP) 328.3 (M+H)$^+$.

Examples 61 and 62

The following compounds are prepared in analogy to Example 1:
60. rac-9,10-Dimethoxy-3β-p-tolyl-1,3,4,6,7,11bβ-hexahydro-2H-pyrido[2,1-a]isoquinolin-2β-ylamine as a yellow powder, MS (ISP) 353.3 (M+H)$^+$.
61. rac-9,10-Dimethoxy-3β-p-tolyl-1,3,4,6,7,11bβ-hexahydro-2H-pyrido[2,1-a]isoquinolin-2α-ylamine as a yellowish powder, MS (ISP) 353.3 (M+H)$^+$.

The educts used in Examples 61 and 62 (compounds of formulae II, III and VI) which have not been described above can be prepared according to the procedures described below or in analogy thereto.

Oxime Derivative (Compound of Formula II)

The following compound is prepared in analogy to the procedure for the preparation of rac-3β-Butyl-9,10-dimethoxy-1,3,4,6,7,11bβ-hexahydro-pyrido[2,1-a]isoquinolin-2-one oxime described in above Example 1:
rac-9,10-Dimethoxy-3β-p-tolyl-1,3,4,6,7,11bβ-hexahydro-pyrido[2,1-a]isoquinolin-2-one oxime as a yellowish powder, MS (ISP) 367.2 (M+H)$^+$.

Ketone Derivative (Compound of Formula III)

The following compound is prepared in analogy to the procedure for the preparation of rac-3β-Butyl-9,10-dimethoxy-1,3,4,6,7,11bβ-hexahydro-pyrido[2,1-a]isoquinolin-2-one described in above Example 1:
rac-9,10-Dimethoxy-3β-p-tolyl-1,3,4,6,7,11b-hexahydro-pyrido[2,1-a]isoquinolin-2-one as an off-white powder, MS (ISP) 352.3 (M+H)$^+$.

Ammonium Iodide Derivative (Compound of Formula V)

A mixture of 4-methylphenylacetone (3.01 g), paraformaldehyde (0.489 g) and dimethylamine hydrochloride (1.49 g) in MeOH (2 ml) is stirred under reflux for 3 h. The reaction mixture is diluted with 20 ml of water and the product is extracted with two portions of ether. After addition of 1 M aqueous NaOH solution, the aqueous layer is extracted with two more portions of ether. The combined organic layers are dried (Na$_2$SO$_4$) and the solvent is evaporated to obtain 4-dimethylamino-3-p-tolyl-butan-2-one (compound of formula VI) as a yellowish liquid, MS (ISP) 206.2 (M+H)$^+$. 4-Dimethylamino-3-p-tolyl-butan-2-one is dissolved in AcOEt (17 ml) and iodomethane (1.46) is added. After 1 h the formed solid is collected by filtration, washed with AcOEt and dried on the vacuum. 2.61 g of trimethyl-(3-oxo-2-p-tolyl-butyl)-ammonium iodide are obtained as an off-white solid, MS (ISP) 220.3 M$^+$.

Examples 63 and 64

(i) 21.5 mg of palladium acetate, 276 mg of sodium tert-butoxide and 23 mg of tri-tert-butylphosphine are placed in a flask, which is evaporated and charged with argon three times. 2 ml of tetrahydrofurane is added under argon. To this solution 177 mg of 4-bromoxylene and 250 mg of rac-9,10-dimethoxy-1,3,4,6,7,11b-hexahydro-2H-benzo[a]quinolizin-2-one (D. Beke, C. Szantay, Chem. Ber. 95, 2132 (1962)) dissolved in 1 ml of tetrahydrofurane are added. The reaction is stirred at room temperature under argon over night. The crude reaction is diluted with diethyl ether, washed with water and sat. aq. sodium chloride solution. The organic layer is dried over sodium sulfate, filtered and the solvent is evaporated. The residue is purified by column chromatography (silica gel, diethyl ether) to yield 92.0 mg of rac-9,10-dimethoxy-3β-(3,4-dimethyl-phenyl)-1,3,4,6,7,11bβ-hexahydro-2H-pyrido[2,1-a]isoquinolin-2-one as a light yellow solid. $^1$H NMR (CDCl$_3$): δ=7.16–6.90 (m, 3 H), 6.64 (s, 1 H), 6.59 (s, 1 H), 3.93–3.71 (m, 8 H, 2 MeO+2 H), 3.40–3.36 (m, 1 H), 3.17–2.6 (m, 7 H), 2.4–2.2 (m, 6 H, 2 Ar—CH$_3$). MS (ISP): 366.2 (M+H)$^+$.

(ii) To a yellow suspension of 86 mg of rac-9,10-dimethoxy-3β-(3,4-dimethyl-phenyl)-1,3,4,6,7,11bβ-hexahydro-pyrido[2,1-a]isoquinolin-2-one in 4 ml of ethanol is added 21.2 mg sodium acetate and 18.0 mg hydroxylamine hydrochloride. The reaction mixture is stirred for four hours at room temperature. 4 ml of water and 150 mg of nickel-aluminum alloy are added. 0.7 ml of an aq. 32% sodium hydroxide solution is added dropwise. The mixture is stirred at room temperature over night, filtered and the solution is extracted three times with dichloromethane. The organic layers are dried over sodium sulfate and the solvent is evaporated. The residue is purified by chromatography (silica gel, dichloro-methane/methanol/sat. aq. ammonia=97/3/0.3). Two products are obtained. They are dissolved independently in dichloromethane and saturated etheral hydrochloric acid solution is added until a solid precipitated.

63. rac-9,10-dimethoxy-3β-(3,4-dimethyl-phenyl)-1,3,4,6,7,11bβ-hexahydro-2H-pyrido[2,1-a]isoquinolin-2β-ylamine chlorohydrate (1:2)

14.4 mg of the title compound are obtained as a light yellow solid. This product is eluted first during chromatography. $^1$H NMR (CDCl$_3$): δ=7.17–6.95 (m, 3 H), 6.70 (s, 1 H), 6.60 (s, 1 H), 3.85 (s, 3 H, MeO), 3, 84 (s, 3 H, MeO), 3.6–2.2 (m, 17 H), 2.0–1.8 (m, 1 H). MS (ISP): 367.3 (M+H)$^+$.

64. rac-9,10-dimethoxy-3β-(3,4-Dimethyl-phenyl)-1,3,4,6,7,11bβ-hexahydro-2H-pyrido[2,1-a]isoquinolin-2α-ylamine chlorohydrate (1:2)

39.5 mg of the title compound are obtained as a light yellow solid. This product is eluted second during chromatography. $^1$H NMR (CDCl$_3$): δ=7.15–6.99 (m, 3 H), 6.75 (s, 1 H), 6.60 (s, 1 H), 3.85 (s, 3 H, Ar—CH$_3$), 3.83 (s, 3 H, MeO), 3.4–2.9 (m, 5 H), 2.7–2.2 (m, 12 H). MS (ISP): 367.3 (M+H)$^+$.

Examples 65–68

The following compounds are prepared in analogy to Examples 63 and 64:

65. rac-9,10-Dimethoxy-3β-(3-methoxy-phenyl)-1,3,4,6,7,11bβ-hexahydro-2H-pyrido[2,1-a]isoquinolin-2β-ylamine chlorohydrate (1:2).

The title compound was obtained as a light yellow solid. This product is eluted first during chromatography. $^1$H NMR (CDCl$_3$): δ=7.29–7.24 (m, 1 H), 6.84–6.74 (m, 3 H), 6.70 (s, 1 H), 6.60 (s, 1 H), 3.94–3.82 (m, 10 H, 3 MeO+1 H), 3.60–2.36 (m., 10 H), 200–1.95 (m, 1 H). MS (ISP): 369.3 (M+H)$^+$.

66. rac-9,10-Dimethoxy-3β-(3-methoxy-phenyl)-1,3,4,6,7,11bβ-hexahydro-2H-pyrido[2,1-a]isoquinolin-2α-ylamine chlorohydrate (1:2).

The title compound was obtained as a light yellow solid. This product is eluted second during chromatography. $^1$H NMR (CDCl$_3$): δ=7.30–7.24 (m, 1 H), 6.89–6.79 (m, 3 H), 6.75 (s, 1 H), 6.60 (s, 1 H), 3.85–3.82 (m, 6 H, 2 MeO), 3.82 (m, 4 H, 1 MeO+1 H), 3.4–2.2 (m, 11 H). MS (ISP): 369.3 (M+H)$^+$.

67. rac-9,10-Dimethoxy-3β-pyridin-1,3,4,6,7,11bβ-hexahydro-2H-pyrido[2,1-a]isoquinolin-2α-ylamine chlorohydrate (1:2).

The title compound is obtained as a light yellow solid. This product is eluted first during chromatography. $^1$H NMR (CDCl$_3$): δ=8.60–8.57 (m, 1 H), 7.68–7.63 (m, 1 H), 7.27–7.15 (m, 2 H), 6.71 (s, 1 H), 6.60 (s, 1 H), 3.85–3.84 (m, 7 H, 2 MeO), 3.8–3.0 (m, 7 H), 2.8–2.6 (m, 1 H), 2.45–2.39 (m, 1 H), 2–1.92 (m, 1 H). MS (ISP): 340.3 (M+H)$^+$.

68. rac-9,10-Dimethoxy-3β-pyridin-1,3,4,6,7,11bβ-hexahydro-2H-pyrido[2,1-a]isoquinolin-2α-ylamine chlorohydrate (1:2).

The title compound was obtained as a light yellow solid. This product is eluted second during chromatography. $^1$H NMR (CDCl$_3$): δ=8.63–8.61 (m, 1 H), 7.68–7.62 (m, 1 H), 7.26–7.16 (m, 2 H), 6.75 (s, 1 H), 6.60 (s, 1 H), 3.87–3.80 (m, 7 H), 3.5–2.5 (m, 11 H). MS (ISP): 340.3 (M+H)$^+$.

The following compounds are prepared in analogy to the procedure used for the preparation of rac-9,10-dimethoxy-3β-(3,4-dimethyl-phenyl)-1,3,4,6,7,11bβ-hexahydro-2H-pyrido[2,1-a]isoquinolin-2-one described above in Examples 63 and 64:

rac-9,10-dimethoxy-3β-(3-methoxy-phenyl)-1,3,4,6,7,11bβ-hexahydro-2H-pyrido[2,1-a]isoquinolin-2-one obtained as a light yellow solid. $^1$H NMR (CDCl$_3$): δ=7.43–6.56 (m, 5 H), 3.95–3.72 (m, 11 H, 3 MeO+2 H), 3.45–3.40 (m, 1 H), 3.2–2.6 (m, 8 H). MS (ISP): 368.3 (M+H)$^+$.

rac-9,10-dimethoxy-3β-pyridin-2-yl-1,3,4,6,7,11bβ-hexahydro-2H-pyrido[2,1-a]isoquinolin-2-one obtained as an orange solid. $^1$H NMR (CDCl$_3$): δ=8.38–8.35 (m, 1 H), 7.72–7.67 (m, 1 H), 7.07–6.96 (m, 2 H), 6.68 (s, 1 H), 6.62 (s, 1 H), 3.93–3.75 (m, 8 H, 2 MeO+2 H), 3.65–3.60 (m, 1 H), 3.40–3.26 (m, 7 H). MS (ISP): 339.3 (M+H)$^+$.

Examples 69–81

The following compounds were prepared in analogy to Example 1:

69. rac-4-(2β-Amino-3β-butyl-9,10-dimethoxy-1,3,4,6,7,11bβ-hexahydro-2H-pyrido[2,1-a]isoquinolin-7β-yl)-phenol, MS (ISP) 411.5 (M+H)$^+$.

70. rac-3β-Butyl-9,10-dimethoxy-6-methyl-1,3,4,6,7,11bβ-hexahydro-2H-pyrido[2,1-a]isoquinolin-2-ylamine, MS (ISP) 333.4 (M+H)$^+$.

71. rac-3β-Butyl-7β-(4-chloro-phenyl)-9,10-dimethoxy-1,3,4,6,7,11bβ-hexahydro-2H-pyrido[2,1-a]isoquinolin-2α-ylamine, MS (ISP) 429.6 (M+H)$^+$.
72. rac-3β-Butyl-7α-(4-chloro-phenyl)-9,10-dimethoxy-1,3,4,6,7,11bβ-hexahydro-2H-pyrido[2,1-a]isoquinolin-2α-ylamine, MS (ISP) 429.6 (M+H)$^+$.
73. rac-3β-Butyl-7β-(3,4-dimethoxy-phenyl)-9,10-dimethoxy-1,3,4,6,7,11bβ-hexahydro-2H-pyrido[2,1-a]isoquinolin-2α-ylamine, MS (ISP) 455.6 (M+H)$^+$.
74. rac-3β-Butyl-9,10-dimethoxy-7,7-dimethyl-1,3,4,6,7,11bβ-hexahydro-2H-pyrido[2,1-a]isoquinolin-2α-ylamine, MS (ISP) 347.5 (M+H)$^+$.
75. rac-3,l-Butyl-9,10-dimethoxy-7,7-dimethyl-1,3,4,6,7,11bβ-hexahydro-2H-pyrido[2,1-a]isoquinolin-2β-ylamine, MS (ISP) 347.5 (M+H)$^+$.
76. rac-7β-Butyl-11,12-dimethoxy-2,3,4,4aβ,6,7,8,9,9aα,13bβ-decahydro-1H-pyrido[1,2-f]phenanthridin-8β-ylamine, MS (ISP) 373.5 (M+H)$^+$.
77. rac-7β-Butyl-11,12-dimethoxy-2,3,4,4aβ,6,7,8,9,9aα13bβ-decahydro-1H-pyrido[1,2-f]phenanthridin-8α-ylamine, MS (ISP) 373.5 (M+H)$^+$.
78. rac-3β-Butyl-7α-(3,4-dimethoxy-phenyl)-9,10-dimethoxy-6α-methyl-1,3,4,6,7,11bβ-hexahydro-2H-pyrido[2,1-a]isoquinolin-2-ylamine, MS (ISP) 411.5 (M+H)$^+$.
79. rac-7β-Butyl-11,12-dimethoxy-13b-methyl-2,3,4,4aβ,6,7,8,9,9a,13b-decahydro-1H-pyrido[1,2-f]phenanthridin-8β-ylamine, MS (ISP) 387.4 (M+H)$^+$.
80. rac-9,10-Dimethoxy-3α-phenyl-1,3,4,6,7,11bα-hexahydro-2H-pyrido[2,1-a]isoquinolin-2α-yl amine, MS (ISP) 339.3 (M+H)$^+$.
81. rac-9,10-Dimethoxy-3α-phenyl-1,3,4,6,7,11bα-hexahydro-2H-pyrido[2,1-a]isoquinolin-2β-yl amine, MS (ISP) 339.4 (M+H)$^+$.

Oxime Derivatives (Compound of Formula II)

The following compounds are prepared in analogy to the procedure used for the preparation of rac-3β-butyl-9,10-dimethoxy-1,3,4,6,7,11bβ-hexahydro-pyrido[2,1-a]isoquinolin-2-one oxime described above in Example 1:

rac-3α-Butyl-9,10-dimethoxy-7α-(4-methoxy-phenyl)-1,3,4,6,7,11bα-hexahydro-pyrido[2,1-a]isoquinolin-2-one oxime, MS (ISP) 439.5 (M+H)$^+$.

rac-7β-Butyl-11,12-dimethoxy-2,3,4,4aβ,6,7,8,9,9aα,13bβ-decahydro-1H-pyrido[1,2-f]phenanthridin-8-one oxime, MS (ISP) 439.5 (M+H)$^+$.

rac-3-Butyl-7-(3,4-dimethoxy-phenyl)-9,10-dimethoxy-6-methyl-1,3,4,6,7,11b-hexahydro-pyrido[2,1-a]isoquinolin-2-one oxime, MS (ISP) 483.5 (M+H)$^+$.

Ketone Derivatives (Compounds of Formula III)

The following compounds are prepared in analogy to the procedure used for the preparation of rac-3β-butyl-9,10-dimethoxy-1,3,4,6,7,11bβ-hexahydro-pyrido[2,1-a]isoquinolin-2-one described above in Example 1:

rac-3β-Butyl-7β-(4-hydroxy-phenyl)-9,10-dimethoxy-1,3,4,6,7,11bβ-hexahydro-pyrido[2,1-a]isoquinolin-2-one, MS (ISP) 410.5 (M+H)$^+$.

rac-3β-Butyl-9,10-dimethoxy-6-methyl-1,3,4,6,7,11bβ-hexahydro-pyrido[2,1-a]isoquinolin-2-one, MS (ISP) 332.5 (M+H)$^+$.

rac-3β-Butyl-7β-(4-chloro-phenyl)-9,10-dimethoxy-1,3,4,6,7,11bβ-hexahydro-pyrido[2,1-a]isoquinolin-2-one, MS (ISP) 438.5 (M+H)$^+$.

rac-3β-Butyl-7β-(3,4-dimethoxy-phenyl)-9,10-dimethoxy-1,3,4,6,7,11bβ-hexahydro-pyrido[2,1-a]isoquinolin-2-one, MS (ISP) 454.5 (M+H)$^+$.

rac-3β-Butyl-9,10-dimethoxy-7β-(4-methoxy-phenyl)-1,3,4,6,7,11bβ-hexahydro-pyrido[2,1-a]isoquinolin-2-one, MS (ISP) 424.5 (M+H)$^+$.

rac-3β-Butyl-9,10-dimethoxy-7,7-dimethyl-1,3,4,6,7,11bβ-hexahydro-pyrido[2,1-a]isoquinolin-2-one, MS (ISP) 346.5 (M+H)$^+$.

rac-7-Butyl-11,12-dimethoxy-1,2,3,4,4a,6,7,9,9a,13b-decahydro-pyrido[1,2-f]phenanthridin-8-one, MS (ISP) 372.5 (M+H)$^+$.

rac-3β-Butyl-7α-(3,4-dimethoxy-phenyl)-9,10-dimethoxy-6α-methyl-1,3,4,6,7,11bβ-hexahydro-pyrido[2,1-a]isoquinolin-2-one, MS (ISP) 467.5 (M+H)$^+$.

rac-7β-Butyl-11,12-dimethoxy-13b-methyl-2,3,4,4aβ,6,7,8,9,9a,13b-decahydro-1H-pyrido[1,2-f]phenanthridin-8-one, MS (ISP) 386.5 (M+H)$^+$.

Synthesis of Dihydroisoquinolines (Compounds of Formula IV)

In analogy to N. Sotomayor, E. Dominguez and E. Lete; Tetrahedron; 51; 12721 (1995).

rac-6,7-Dimethoxy-4,4-dimethyl-3,4-dihydro-isoquinoline

A solution of 1.0 g of 1,2,3,4-tetrahydro-6,7-dimethoxy-4,4-dimethyl-isoquinoline in 100 ml of ethanol is treated with 2.3 g of iodine and 0.49 g of sodium acetate and heated under reflux for 1 hour. The reaction mixture is cooled down and 30 ml of a 10% sodium thiosulphate-solution is added. The mixture is then diluted with water and extracted with dichloromethane (2×100 ml). The combined organic extracts are washed with brine, dried over sodium sulfate and concentrated in vacuo. The foamy residue is purified by chromatography (SiO$_2$, dichloromethane-1% ammonia in methanol, 0–12%) to give the title compound as a yellowish oil (0.72 g), MS (ISP) 220.4 (M+H)$^+$.

rac-4-(4-Chloro-phenyl)-6,7-dimethoxy-3,4-dihydro-isoquinoline, MS (ISP) 302.3 (M+H)$^+$.

rac-4-(3,4-Dimethoxy-phenyl)-6,7-dimethoxy-3,4-dihydro-isoquinoline, MS (ISP) 328.4 (M+H)$^+$.

rac-6,7-Dimethoxy-4-(4-methoxy-phenyl)-3,4-dihydro-isoquinoline, MS (ISP) 298.4 (M+H)$^+$.

rac-4α-(3,4-Dimethoxy-phenyl)-6,7-dimethoxy-3α-methyl-3,4-dihydro-isoquinoline, MS (ISP) 342.3 (M+H)$^+$.

rac-8,9-Dimethoxy-10b-methyl-1,2,3,4,4a,10b-hexahydro-phenanthridine, MS (ISP) 250.4 (M+H)$^+$.

Examples 82–85

The following enantiopure amines were obtained from the corresponding enantiopure ketones in analogy to Example 1.

82. 9,10-Dimethoxy-3α-phenyl-1,3,4,6,7,11bα-hexahydro-2H-pyrido[2,1-a]isoquinolin-2α-yl amine, MS (ISP) 339.3 (M+H)$^+$.
83. 9,10-Dimethoxy-3α-phenyl-1,3,4,6,7,11bα-hexahydro-2H-pyrido[2,1-a]isoquinolin-2β-yl amine, MS (ISP) 339.3 (M+H)$^+$.
84. 9,10-Dimethoxy-3β-phenyl-1,3,4,6,7,11bβ-hexahydro-2H-pyrido[2,1-a]isoquinolin-2β-yl amine, MS (ISP) 339.3 (M+H)$^+$.
85. 9,10-Dimethoxy-3β-phenyl-1,3,4,6,7,11bβ-hexahydro-2H-pyrido[2,1-a]isoquinolin-2α-yl amine, MS (ISP) 339.3 (M+H)$^+$.

Ketone Derivatives (Compounds of Formula III)

(−/trans)-9,10-Dimethoxy-3-phenyl-1,3,4,6,7,11b-hexahydro-pyrido[2,1-a]isoquinolin-2-one$[α]_D^{20}$=−46.3 (c0.28, CHCl$_3$, λ=436 nm) and (+/trans)-9,10-Dimethoxy-3-phenyl-1,3,4,6,7,11b-hexahydro-pyrido[2,1-a]isoquinolin-2-one ($[α]_D^{20}$=+44.8(c0.28, CHCl$_3$, λ=436 nm)

were obtained by chiral separation of the corresponding racemic mixture rac-9,10-Dimethoxy-3-phenyl-1,3,4,6,7,11b-hexahydro-pyrido[2,1-a]isoquinolin-2-one using Chiracel OD (20 μm, 25 cm×5 cm), eluting with Heptan/EtOH/DEA (80/20/0.01 at 80 ml/min).

Example 86

(6S)-(2-Amino-3-butyl-9,10-dimethoxy-1,3,4,6,7,11b-hexahydro-2H-pyrido[2,1-a]isoquinolin-6-yl)-methanol was obtained from (6S)-3-Butyl-6-hydroxymethyl-9,10-dimethoxy-1,3,4,6,7,11b-hexahydro-pyrido[2,1-a]isoquinolin-2-one in analogy to Example 1.

(6S)-3-Butyl-6-hydroxymethyl-9,10-dimethoxy-1,3,4,6,7,11b-hexahydro-pyrido[2,1-a]isoquinolin-2-one.

(i) A solution of 1.4 g (S)-6,7-Dimethoxy-3-tert-butyldimethoxysiloxymethyl-3,4-dihydroisoquinoline (Y. Haraguchi, Kozima, S. Yamaguchi, R. Tetrahedron Asymmetry, 1996, 7, 443) in 8.5 ml of methanol is treated with 1.37 g of (2-acetylhexyl)trimethyl-ammonium iodid and heated under reflux for 4 hours. After such time another 0.7 g of (2-acetylhexyl)trimethylammonium iodid was added and the reaction mixture was stirred under reflux for another 20 hours. The reaction mixture is cooled down and treated with a solution of 0.76 g of potassium hydroxide in 70 ml of water. The ethanol is evaporated and the aq. solution is extracted three times with 15 ml of dichloromethane.

The combined organic extracts are dried over anhydrous sodium sulfate and evaporated. The residue is purified by chromatography (silica gel, hexane/ethyl acetate 0–100%) to give 1.95 g of (6S)-3-Butyl-3-hydroxy-6-tert-butyldimethoxysiloxymethyl-9,10-dimethoxy-1,3,4,6,7,11b-hexahydro-pyrido[2,1-a]isoquinolin-2-one as a mixture of diasteomers, MS (ISP) 462.5 (M+H)$^+$.

(ii) To a solution of 0.40 g of (6S)-3-Butyl-3-hydroxy-6-tert-butyldimethoxy-siloxymethyl-9,10-dimethoxy-1,3,4,6,7,11b-hexahydro-pyrido[2,1-a]isoquinolin-2-one in 13 ml of THF at 0° C. was slowly added a solution of 1.78 ml of tetrabutylammonium fluoride (1M in THF). The reaction mixture was stirred for 2 hours keeping the temperature between 0–5° C. The reaction mixture was poured into ice cooled water (49 ml) and then extracted two times with 30 ml of ethyl acetate. The organic extracts were dried over anhydrous sodium sulfate and concentrated in vacuo. The residue was then purified by chromatography (silica gel, hexane/ethyl acetate 0–70%) to give 0.30 g of (6S)-3-Butyl-6-hydroxymethyl-9,10-dimethoxy-1,3,4,6,7,11b-hexahydro-pyrido[2,1-a]isoquinolin-2-one, MS (ISP) 348.3 (M+H)$^+$.

Examples 87–102

The Following Compounds Were Prepared in Analogy to Example 19:

87. rac-4-(2β-Amino-3β-butyl-9,10-dimethoxy-1,3,4,6,7,11bβ-hexahydro-2H-pyrido[2,1-a]isoquinolin-7-yl)-phenol hydrochloride, MS (ISP) 411.5 (M+H)$^+$.
88. rac-4-(2β-Amino-3β-butyl-9,10-dimethoxy-1,3,4,6,7,11bβ-hexahydro-2H-pyrido[2,1-a]isoquinolin-7β-yl)-phenol hydrochloride, MS (ISP) 411.4 (M+H)$^+$.
89. rac-3β-Butyl-9,10-dimethoxy-6-methyl-1,3,4,6,7,11bβ-hexahydro-2H-pyrido[2,1-a]isoquinolin-2-ylamine hydrochloride, MS (ISP) 333.4 (M+H)$^+$.
90. rac-3β-Butyl-7β-(4-chloro-phenyl)-9,10-dimethoxy-1,3,4,6,7,11bβ-hexahydro-2H-pyrido[2,1-a]isoquinolin-2α-ylamine hydrochloride, MS (ISP) 429.6 (M+H)$^+$.
91. rac-3β-Butyl-7α-(4-chloro-phenyl)-9,10-dimethoxy-1,3,4,6,7,11b, β-hexahydro-2H-pyrido[2,1-a]isoquinolin-2α-ylamine hydrochloride, MS (ISP) 429.6 (M+H)$^+$.
92. rac-3β-Butyl-7β-(3,4-dimethoxy-phenyl)-9,10-dimethoxy-1,3,4,6,7,11bβ-hexahydro-2H-pyrido[2,1-a]isoquinolin-2α-ylamine hydrochloride, MS (ISP) 455.6 (M+H)$^+$.
93. rac-3α-Butyl-7β-(3,4-dimethoxy-phenyl)-9,10-dimethoxy-1,3,4,6,7,11bβ-hexahydro-2H-pyrid o[2,1-a]isoquinolin-2β-ylamine hydrochloride, MS (ISP) 455.6 (M+H)$^+$.
94. rac-3β-Butyl-7β-(3,4-dimethoxy-phenyl)-9,10-dimethoxy-1,3,4,6,7,11bβ-hexahydro-2H-pyrido[2,1-a]isoquinolin-2β-ylamine hydrochloride, MS (ISP) 455.6 (M+H)$^+$.
95. rac-3β-Butyl-7α-(3,4-dimethoxy-phenyl)-9,10-dimethoxy-1,3,4,6,7,11bβ-hexahydro-2H-pyrido[2,1-a]isoquinolin-2α-ylamine hydrochloride, MS (ISP) 455.6 (M+H)$^+$.
96. rac-3β-Butyl-9,10-dimethoxy-7β-(4-methoxy-phenyl)-1,3,4,6,7,11bβ-hexahydro-2H-pyrido[2,1-a]isoquinolin-2α-ylamine hydrochloride, MS (ISP) 425.5 (M+H)$^+$.
97. rac-3β-Butyl-9,10-dimethoxy-7β-(4-methoxy-phenyl)-1,3,4,6,7,11bβ-hexahydro-2H-pyrido[2,1-a]isoquinolin-2β-ylamine hydrochloride, MS (ISP) 425.5 (M+H)$^+$.
98. rac-3β-Butyl-9,10-dimethoxy-7,7-dimethyl-1,3,4,6,7,11bβ-hexahydro-2H-pyrido[2,1-a]isoquinolin-2α-ylamine hydrochloride, MS (ISP) 347.5 (M+H)$^+$.
99. rac-3β-Butyl-9,10-dimethoxy-7,7-dimethyl-1,3,4,6,7,11bβ-hexahydro-2H-pyrido[2,1-a]isoquinolin-2β-ylamine hydrochloride, MS (ISP) 347.5 (M+H)$^+$.
100. rac-7β-Butyl-11,12-dimethoxy-2,3,4,4aβ,6,7,8,9,9aα,13bβ-decahydro-1H-pyrido[1,2-f]phenanthridin-8β-ylamine hydrochloride, MS (ISP) 373.5 (M+H)$^+$.
101. rac-7β-Butyl-11,12-dimethoxy-2,3,4,4aβ,6,7,8,9,9aα13bβ-decahydro-1H-pyrido[1,2-f]phenanthridin-8α-ylamine hydrochloride, MS (ISP) 373.5 (M+H)$^+$.
102. rac-3β-Butyl-7α-(3,4-dimethoxy-phenyl)-9,10-dimethoxy-6α-methyl-1,3,4,6,7,11bβ-hexahydro-2H-pyrido[2,1-a]isoquinolin-2-ylamine hydrochloride, MS (ISP) 411.5 (M+H)$^+$.

Galenical Examples

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |

| Ingredients | Per tablet | |
|---|---|---|
| Iron oxyde (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |

| Karion 83 | 8.0 mg (dry matter) |
|---|---|
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesium stearate and the flavouring additives and filled into sachets.

What is claimed is:

1. A compound of formula (I)

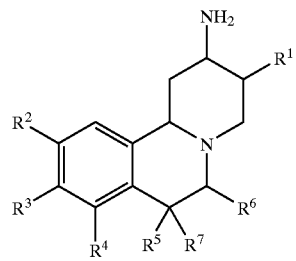

(I)

wherein $R^1$ is aryl, substituted aryl, heteroaryl, or substituted heteroaryl;

$R^2$, $R^3$ and $R^4$ are each independently hydrogen, halogen, hydroxy, lower alkyl, lower alkoxy or lower alkenyl, wherein lower alkyl, lower alkoxy and lower alkenyl are optionally substituted by lower alkoxycarbonyl, aryl, substituted aryl, heterocyclyl or substituted heterocyclyl.

$R^5$ is hydrogen, fluorine, lower alkyl, -aryl or substituted aryl;

$R^6$ is hydrogen, lower alkyl or hydroxy-lower alkyl, or $R^5$ and $R^6$ together with the carbon atoms to which they are attached form a five or six membered saturated carbocyclic ring;

$R^7$ is hydrogen, fluorine or lower alkyl;

wherein substituted aryl is aryl that is mono-, di- or tri-substituted by lower alkyl, lower alkoxy, halo, cyano, azido, amino, di-lower alkyl amino or hydroxy;

substituted heteroaryl is heteroaryl that is mono-, di- or tri-substituted by halogen, amino, perfluoro-lower alkyl, lower alkyl or lower alkoxy;

substituted heterocyclyl is heterocyclyl that is mono-, di- or tri-substituted by lower alkyl, lower alkoxy, halo, cyano, azido, amino, di-lower alkyl amino or hydroxyl; and pharmaceutically acceptable salts thereof.

2. The compound according to claim 1, wherein $R^1$ is aryl, or substituted aryl;

$R^2$, $R^3$ and $R^4$ are each independently hydrogen, hydroxy, lower alkyl, lower alkoxy or lower alkenyl, wherein lower alkyl, lower alkoxy and lower alkenyl are optionally substituted by lower alkoxycarbonyl, aryl, substituted aryl, heterocyclyl, or substituted heterocyclyl;

$R^5$ $R^6$ are each independently hydrogen, lower alkyl, aryl, substituted aryl, or, together with the carbon atoms to which they are attached form a five or six membered saturated carbocyclic ring.

3. The compound according to claim 1, wherein $R^1$ is phenyl, or lower alkyl substituted by cycloalkyl.

4. The compound according to claim 3, wherein $R^1$ is lower alkyl or lower alkyl substituted by cycloalkyl.

5. The compound according to claim 1, wherein $R^1$ is a heteroaryl or substituted heteroaryl in which the heteroaryl residue is selected from pyrrolyl and pyridinyl.

6. The compound according to claim 1, wherein $R^2$, $R^3$ and $R^4$ are each independently hydrogen, hydroxy, lower alkoxy; or lower alkoxy substituted by aryl, substituted aryl, heterocyclyl, substituted heterocyclyl, or lower alkoxycarbonyl.

7. The compound according to claim 6, wherein $R^2$, $R^3$ and $R^4$ are each independently lower alkoxy substituted by phenyl or phenyl substituted by di-lower alkyl amino or cyano.

8. The compound according to claim 6, wherein $R^2$ is lower alkoxy.

9. The compound according to claim 6, wherein $R^3$ is lower alkoxy, hydrogen, hydroxy; or lower alkoxy substituted by aryl, substituted aryl, heterocyclyl, substituted heterocyclyl or lower alkoxycarbonyl.

10. The compound according to claim 9, wherein $R^3$ is lower alkoxy, hydrogen or hydroxy.

11. The compound according to claim 6, wherein $R^4$ is lower alkoxy, hydrogen or hydroxy.

12. The compound according to claim 1, wherein $R^5$ and $R^6$ are hydrogen or, together with the carbon atoms to which they are attached, form a six membered saturated carbocyclic ring.

13. The compound according to claim 1, rac-9,10-dimethoxy-3β-phenyl-1,3,4,6,7,11bβhexahydro-2H-pyrido[2,1-a]isoquinolin-2-ylamine, or a pharmaceutically acceptable salt thereof.

14. The compound according to claim 1, selected from the group consisting of:

rac-9,10-Dimethoxy-3β-pyrrol-1-yl-1,3,4,6,7, 11bβ-hexahydro-2H-pyrido[2,1-a]isoquinolin-2α-ylamine, rac-9,10-Dimethoxy-3β-p-tolyl-1,3,4,6,7,11bβ-hexahydro-2H-pyrido[2,1-a]isoquinolin-2β-ylamine, rac-9,10-Dimethoxy-3β-p-tolyl-1,3,4,6,7, 11bα-hexahydro-2H-pyrido[2,1-a]isoquinolin-2α-ylamine, rac-9,10-dimethoxy-3β-(3,4-dimethyl-phenyl)-1,3,4,6,7, 11bβ-hexahydro-2H-pyrido[2,1-a]isoquinolin-2β-ylamine chlorohydrate (1:2), rac-9,10-dimethoxy-3β-(3,4-Dimethyl-phenyl)-1,3,4,6,7, 11bβ-hexahydro-2H-pyrido[2,1-a]isoquinolin-2α-ylamine chlorohydrate (1:2), rac-9,10-Dimethoxy-3β-(3-methoxy-phenyl)-1,3,4,6,7, 11bβ-hexahydro-2H-pyrido[2,1-a]isoquinolin-2β-ylamine chlorohydrate (1:2), rac-9,10-Dimethoxy-3β-(3-methoxy-phenyl)-1,3,4,6,7, 11bβ-hexahydro-2H-pyrido[2,1-a]isoquinolin-2α-ylamine chlorohydrate (1:2), rac-9,10-Dimethoxy-3β-pyridin-1,3,4,6,7,11bβ-hexahydro-2H-pyrido[2,1-a]isoquinolin-2β-ylamine chlorohydrate (1:2), rac-9,10-Dimethoxy-3β-pyridin-1,3,4,6,7,11bβ-hexahydro-2H-pyrido[2,1-a]isoquinolin-2α-ylamine chlorohydrate (1:2), rac-9,10-Dimethoxy-3α-phenyl-1,3,4,6,7,11bα-hexahydro-2H-pyrido[2,1-a]isoquinolin-2α-yl amine, rac-9,10-Dimethoxy-3α-phenyl-1,3,4,6,7,11bα-hexahydro-2H-pyrido[2,1-a]isoquinolin-2β-yl amine, 9,10-Dimethoxy-3α-phenyl-1,3,4,6,7,11bα-hexahydro-2H-pyrido[2,1-a]isoquinolin-2α-yl amine, 9,10-Dimethoxy-3α-phenyl-1,3,4,6,7,11bα-hexahydro-2H-pyrido[2,1-a]isoquinolin-2β-yl amine, 9,10-Dimethoxy-3β-phenyl-1,3,4,6,7,11bβ-hexahydro-2H-pyrido[2,1-a]isoquinolin-2β-yl amine, 9,10-Dimethoxy-3β-phenyl-1,3,4,6,7,11bβ-hexahydro-2H-pyrido[2,1-a]isoquinolin-2α-yl amine, (6S)-(2-Amino-3-butyl-9,10-dimethoxy-1,3,4,6,7,11b-hexahydro-2H-pyrido[2,1-a]isoquinolin-6-yl)-methanol, rac-4-(2β-Amino-3β-butyl-9,10-dimethoxy-1,3,4,6,7, 11bβ-hexahydro-2H-pyrido[2,1-a]isoquinolin-7-yl)-phenol, rac-4-(2β-Amino-3β-butyl-9,10-dimethoxy-1,3,4,6,7, 11bβ-hexahydro-2H-pyrido[2,1-a]isoquinolin-7β-yl)-phenol, rac-3β-Butyl-9,10-dimethoxy-6-methyl-1,3,4,6,7,11bβ-hexahydro-2H-pyrido[2,1-a]isoquinolin-2-ylamine, rac-3β-Butyl-7β-(4-chloro-phenyl)-9,10-dimethoxy-1,3, 4,6,7,11bβ-hexahydro-2H-pyrido[2,1-a]isoquinolin-2α-ylamine, rac-3β-Butyl-7α-(4-chloro-phenyl)-9,10-dimethoxy-1,3, 4,6,7,11bβ-hexahydro-2H-pyrido[2,1-a]isoquinolin-2α-ylamine, rac-3β-Butyl-7β-(3,4-dimethoxy-phenyl)-9,10-dimethoxy-1,3,4,6,7,11bβ-hexahydro-2H-pyrido[2,1-a]isoquinolin-2α-ylamine, rac-3α-Butyl-7β-(3,4-dimethoxy-phenyl)-9,10-dimethoxy-1,3,4,6,7,11bβ-hexahydro-2H-pyrido[2,1-a]isoquinolin-2β-ylamine, rac-3β-Butyl-7β-(3,4-dimethoxy-phenyl)-9,10-dimethoxy-1,3,4,6,7,11bβ-hexahydro-2H-pyrido[2,1-a]isoquinolin-2β-ylamine, rac-3β-Butyl-7α-(3,4-dimethoxy-phenyl)-9,10-dimethoxy-1,3,4,6,7,1bβ-hexahydro-2H-pyrido[2,1-a]isoquinolin-2α-ylamine, rac-3β-Butyl-9,10-dimethoxy-7β-(4-methoxy-phenyl)-1, 3,4,6,7,11bβ-hexahydro-2H-pyrido[2,1-a]isoquinolin-2α-ylamine, rac-3β-Butyl-9,10-dimethoxy-7β-(4-methoxy-phenyl)-1, 3,4,6,7,11bβ-hexahydro-2H-pyrido[2,1-a]isoquinolin-2α-ylamine, rac-3β-Butyl-9,10-dimethoxy-7,7-dimethyl-1,3,4,6,7, 11bβ-hexahydro-2H-pyrido[2,1-a]isoquinolin-2α-ylamine, rac-3β-Butyl-9,10-dimethoxy-7,7-dimethyl-1,3,4,6,7, 11bβ-hexahydro-2H-pyrido[2,1-a]isoquinolin-2β-ylamine, rac-7β-Butyl-11,12-dimethoxy-2,3,4,4aβ,6,7,8,9,9aα, 13bβ-decahydro-1H-pyrido[1,2-f]phenanthridin-8β-ylamine, rac-7β-Butyl-11,12-dimethoxy-2,3,4,4aβ,6,7,8,9,
9aα13bβ-decahydro-1H-pyrido[1,2-f]phenanthridin-
8α-ylamine, and rac-3β-Butyl-7α-(3,4-dimethoxy-phenyl)-9,10-
dimethoxy-6α-methyl-1,3,4,6,7,11bβ-hexahydro-2H-
pyrido[2,1-a]isoquinolin-2-ylamine;

or a pharmaceutically acceptable salt thereof.

15. A pharmaceutical composition comprising a compound according to claim 1 and a pharmaceutically acceptable carrier.

16. A method for the treatment or prophylaxis of diabetes or non-insulin dependent diabetes mellitus, which comprises administering to a patient in need of treatment a compound according to claim 1 in an amount of from about 1 to 1000 mg per day.

17. The method according to claim 16, wherein the amount administered is a daily dosage of from about 1 to 100 mg.

* * * * *

UNITED STATES PATENT AND TRADEMARK OFFICE
CERTIFICATE OF CORRECTION

| | | |
|---|---|---|
| PATENT NO. | : 6,727,261 B2 | |
| APPLICATION NO. | : 10/321692 | |
| DATED | : April 27, 2004 | |
| INVENTOR(S) | : L. Gobbi et al. | |

It is certified that error appears in the above-identified patent and that said Letters Patent is hereby corrected as shown below:

Title Page
(73)  Assignee: Hoffman-La Roche Inc., Nutley, NJ

Should be

(73)  Assignee: Hoffmann-La Roche Inc. Nutley, NJ

Page 31, Line 17, Claim 3:

"...wherein R1 is phenyl, or lower alkyl substituted by cycloalkyl."

Should be
"...wherein R1 is phenyl."

Page 32, Line 22, Claim 14:

Delete the following:

(6$S$)-(2-Amino-3-butyl-9,10-dimethoxy-1,3,4,6,7,11b-hexahydro-2H-pyrido[2,1-a]isoquinolin-6-yl)-methanol,
*rac*-4-(2β-Amino-3β-butyl-9,10-dimethoxy-1,3,4,6,7,11bβ-hexahydro-2H-pyrido[2,1-a]isoquinolin-7-yl)-phenol,
*rac*-4-(2β-Amino-3β-butyl-9,10-dimethoxy-1,3,4,6,7,11bβ-hexahydro-2H-pyrido[2,1-a]isoquinolin-7β-yl)-phenol,
*rac*-3β-Butyl-9,10-dimethoxy-6-methyl-1,3,4,6,7,11bβ-hexahydro-2H-pyrido[2,1-a]isoquinolin-2-ylamine,
*rac*-3β-Butyl-7β-(4-chloro-phenyl)-9,10-dimethoxy-1,3,4,6,7,11bβ-hexahydro-2H-pyrido[2,1-a]isoquinolin-2α-ylamine,
*rac*-3β-Butyl-7α-(4-chloro-phenyl)-9,10-dimethoxy-1,3,4,6,7,11bβ-hexahydro-2H-pyrido[2,1-a]isoquinolin-2α-ylamine,

UNITED STATES PATENT AND TRADEMARK OFFICE
CERTIFICATE OF CORRECTION

| | |
|---|---|
| PATENT NO. | : 6,727,261 B2 |
| APPLICATION NO. | : 10/321692 |
| DATED | : April 27, 2004 |
| INVENTOR(S) | : L. Gobbi et al. |

It is certified that error appears in the above-identified patent and that said Letters Patent is hereby corrected as shown below:

Page 32, Line 40

Delete the following:

*rac*-3β-Butyl-7β-(3,4-dimethoxy-phenyl)-9,10-dimethoxy-1,3,4,6,7,11bβ-hexahydro-2H-pyrido[2,1-a]isoquinolin-2α-ylamine,
*rac*-3α-Butyl-7β-(3,4-dimethoxy-phenyl)-9,10-dimethoxy-1,3,4,6,7,11bβ-hexahydro-2H-pyrid o[2,1-a]isoquinolin-2β-ylamine,
*rac*-3β-Butyl-7β-(3,4-dimethoxy-phenyl)-9,10-dimethoxy-1,3,4,6,7,11bβ-hexahydro-2H-pyrido[2,1-a]isoquinolin-2β-ylamine,
*rac*-3β-Butyl-7α-(3,4-dimethoxy-phenyl)-9,10-dimethoxy-1,3,4,6,7,11bβ-hexahydro-2H-pyrido[2,1-a]isoquinolin-2α-ylamine,
*rac*-3β-Butyl-9,10-dimethoxy-7β-(4-methoxy-phenyl)-1,3,4,6,7,11bβ-hexahydro-2H-pyrido[2,1-a]isoquinolin-2α-ylamine,
*rac*-3β-Butyl-9,10-dimethoxy-7β-(4-methoxy-phenyl)-1,3,4,6,7,11bβ-hexahydro-2H-pyrido[2,1-a]isoquinolin-2α-ylamine,

UNITED STATES PATENT AND TRADEMARK OFFICE
CERTIFICATE OF CORRECTION

PATENT NO. : 6,727,261 B2
APPLICATION NO. : 10/321692
DATED : April 27, 2004
INVENTOR(S) : L. Gobbi et al.

It is certified that error appears in the above-identified patent and that said Letters Patent is hereby corrected as shown below:

Page 32, Line 59

Delete the following:

*rac*-3β-Butyl-9,10-dimethoxy-7,7-dimethyl-1,3,4,6,7,11bβ-hexahydro-2H-pyrido[2,1-a]isoq uinolin-2α-ylamine,
*rac*-3β-Butyl-9,10-dimethoxy-7,7-dimethyl-1,3,4,6,7,11bβ-hexahydro-2H-pyrido[2,1-a]isoquinolin-2β-ylamine,
*rac*-7β-Butyl-11,12-dimethoxy-2,3,4,4aβ,6,7,8,9,9aα,13bβ-decahydro-1H-pyrido[1,2-f]phenanthridin-8β-ylamine,
*rac*-7β-Butyl-11,12-dimethoxy-2,3,4,4aβ,6,7,8,9,9aα13bβ-decahydro-1H-pyrido[1,2-f]phenanthridin-8α-ylamine, and
*rac*-3β-Butyl-7α-(3,4-dimethoxy-phenyl)-9,10-dimethoxy-6α-methyl-1,3,4,6,7,11bβ-hexahydro-2H-pyrido[2,1-a]isoquinolin-2-ylamine;

Signed and Sealed this

Fifth Day of September, 2006

JON W. DUDAS
*Director of the United States Patent and Trademark Office*